(12) United States Patent
Jessee et al.

(10) Patent No.: US 8,759,499 B2
(45) Date of Patent: *Jun. 24, 2014

(54) LIPIDS FOR TRANSFECTION OF EUKARYOTIC CELLS

(75) Inventors: Joel Jessee, Mount Airy, MD (US); Gulilat Gebeyehu, Potomac, MD (US)

(73) Assignee: Molecular Transfer, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,972

(22) Filed: Mar. 28, 2011

(65) Prior Publication Data

US 2012/0052574 A1    Mar. 1, 2012

Related U.S. Application Data

(63) Continuation of application No. 11/434,765, filed on May 17, 2006, now Pat. No. 7,915,230.

(60) Provisional application No. 60/746,858, filed on May 9, 2006, provisional application No. 60/746,854, filed on May 9, 2006, provisional application No. 60/746,594, filed on May 5, 2006, provisional application No. 60/746,604, filed on May 5, 2006, provisional application No. 60/746,424, filed on May 4, 2006, provisional application No. 60/771,864, filed on Feb. 10, 2006, provisional application No. 60/771,865, filed on Feb. 10, 2006, provisional application No. 60/681,462, filed on May 17, 2005.

(51) Int. Cl.
| | |
|---|---|
| *C07D 487/00* | (2006.01) |
| *A61K 48/00* | (2006.01) |
| *A61K 51/00* | (2006.01) |
| *A61K 36/14* | (2006.01) |
| *A01N 63/00* | (2006.01) |

(52) U.S. Cl.
USPC ............ 532/1; 514/44 R; 424/93.2; 424/1.21

(58) Field of Classification Search
CPC ..... A61K 9/1271; A61K 9/127; C21N 15/87; C21N 2720/12022; C07K 14/005; C07C 223/02
See application file for complete search history.

(56) References Cited

U.S. PATENT DOCUMENTS 7,915,230 B2 *   3/2011   Jessee et al. ................ 514/44 R

OTHER PUBLICATIONS

Ryckebusch, et al. (2003) "Synthesis and Antimalarial Evaluation of New 1,4(bis(3-aminopropyl) piperazine Derivatives", Bioorganic & Medicinal Chemistry Letters, 13: 3783-87.*
Balazs, et al. (2011) "Liposomes for Use in Gene Delivery", Journal of Drug Delivery, 2011: pp. 1-12.*

* cited by examiner

*Primary Examiner* — Robert M Kelly
(74) *Attorney, Agent, or Firm* — Perkins Coie LLP

(57) ABSTRACT

Compositions and methods for improved delivery of macromolecules into eukaryotic cells are provided. Fusogenic peptides from fusion proteins of non-enveloped viruses enhance the efficiency of transfection of eukaryotic cells mediated by transfection agents such as cationic lipids, polycationic polymers such as PEI and dendrimers. These fusogenic peptides are used as part of a transfection complex that efficiently delivers a macromolecule, for example, a nucleic acid, into a eukaryotic cell. Novel cationic lipids and compositions of cationic lipids also are provided that may be used for the introduction of macromolecules such as nucleic acids, proteins and peptides into a variety of cells and tissues. The lipids can be used alone, in combination with other lipids and/or in combination with fusogenic peptides to prepare transfection complexes.

24 Claims, 9 Drawing Sheets

Cos-7, ONPG Assay

LIPIDS FOR TRANSFECTION OF EUKARYOTIC CELLS

This application is a continuation of U.S. Ser. No. 11/434,765 filed May 17, 2006, now U.S. Pat. No. 7,915,230, which claims priority to Provisional Application Ser. Nos. 60/746,858 filed May 9, 2006; 60/746,854 filed May 9, 2006; 60/746,594 filed May 5, 2006; 60/746,604 filed May 5, 2006; 60/746,424 filed May 4, 2006; 60/771,864 filed Feb. 10, 2006; 60/771,865 filed Feb. 10, 2006; and 60/681,462 filed May 17, 2005, the contents of each of which are hereby incorporated by reference in their entireties.

BACKGROUND OF THE INVENTION

Lipid aggregates such as liposomes can facilitate introduction of macromolecules, such as DNA, RNA, and proteins, into living cells. Aggregates comprising cationic lipid components can be used to effect delivery of large anionic molecules, such as nucleic acids, into certain types of cells. See Feigner et al., *Nature* 337:387-388 (1989); *Proc. Natl. Acad. Sci. USA* 84:7413 (1987).

The use of cationic lipids has become increasingly popular since its introduction over 15 years ago. Several cationic lipids have been described in the literature and some of these are commercially available. DOTMA (N-[1-(2,3-dioleyloxy)propyl]-N,N,N-trimethylammonium chloride) was the first cationic lipid to be synthesized for the purpose of nucleic acid transfection. See Feigner et al. (*Proc. Nat'l Acad. Sci.* 84, 7413 (1987); U.S. Pat. No. 4,897,355). DOTMA can be formulated alone or can be combined with DOPE (dioleoylphosphatidylethanolamine) into a liposome, and such liposomes can be used to deliver plasmids into some cells. Other classes of lipids subsequently have been synthesized by various groups. For example, DOGS (5-carboxyspermylglycinedioctadecylamide) was the first polycationic lipid to be prepared (Behr et al. *Proc. Nat'l Acad. Sci.* 86, 6982 (1989); U.S. Pat. No. 5,171,678) and other polycationic lipids have since been prepared. The lipid DOSPA (2,3-dioleyloxy-N-[2(sperminecarboxamido)ethyl]-N,N-dimethyl-1-propanaminium) has been described as an effective delivery agent (U.S. Pat. No. 5,334,761).

In other examples, cholesterol-based cationic lipids, such as DC-Chol (N,N-dimethyl-N-ethylcarboxamidocholesterol) have been prepared and used for transfection (Gao et al. *Biochem. Biophys. Res. Comm.* 179, 280 (1991)). In another example 1,4-bis(3-N-oleylamino-propyl)piperazine was prepared and combined with histone H1 to generate a delivery reagent that was reported to be less toxic than other reagents (Wolf et al. *BioTechniques* 23, 139 (1997); U.S. Pat. No. 5,744,335). Several reagents are commercially available. Some examples include Lipofectin® (DOTMA:DOPE) (Invitrogen, Carlsbad, Calif.), LipofectAmine™ (DOSPA:DOPE) (Invitrogen), LipofectAmine2000™ (Invitrogen) Fugene®, Transfectam® (DOGS), Effectene®, and DC-Chol. None of these reagents can be used universally for all cells. This is perhaps not surprising in light of the variation in composition of the membranes of different types of cells as well as the barriers that can restrict entry of extracellular material into cells. Moreover, the mechanism by which cationic lipids deliver nucleic acids into cells is not clearly understood. The reagents are less efficient than viral delivery methods and are toxic to cells, although the degree of toxicity varies from reagent to reagent.

However, transfection agents, including cationic lipids, are not universally effective in all cell types. Effectiveness of transfection of different cells depends on the particular transfection agent composition. In general, polycationic lipids are more efficient than monocationic lipids in transfecting eukaryotic cells. In many cases, cationic lipids alone are not effective or are only partially effective for transfection.

Many biological materials are taken up by cells via receptor-mediated endocytosis, in which a ligand binds to a cell-surface receptor, leading to clustering of ligand-bound receptors, and formation of coated pits followed by internalization of the ligands into endosomes. Both enveloped viruses, like influenza virus and alphaviruses, and non-enveloped viruses, like Adenovirus, infect cells via endocytotic mechanisms. See: Pastan, I. et al. (1986) in "Virus Attachment and Entry into Cells", (Crowell, R. L. and Lonberg-Holm, K., eds.) Am. Soc. Microbiology, Washington, p. 141-146; Kielian et al., (1986) "Entry of Alphaviruses" in The Togaviridae and Flaviviridae, (Schlesinger, S, and Schlesinger, M. J., eds.) Plenum Press, New York p. 91-119; FitzGerald et al. (1983) *Cell* 32:607-617. Enhancement of dendrimer-mediated transfection of some cells by chloroquine (a lysosomotropic agent) suggests that endocytosis is involved in at least some transfections.

Introduction of foreign DNA sequences into eukaryotic cells mediated by viral infection is generally orders of magnitude more efficient than transfection with anionic lipids, cationic lipid, PEI, peptides, or dendrimer transfection agents. Viral infection of all the cells in a culture requires fewer than 10 virus particles per cell. Although the detailed mechanism of fusion is not fully understood and varies among viruses, viral fusion typically involves specific fusogenic agents, such as viral proteins, viral spike glycoproteins and peptides of viral spike glycoproteins. Cell binding and internalization also can be enhanced, accelerated or made selective with peptides that bind cell receptors. For example, the penton-base protein of the Adenovirus coat contains the peptide motif RGD (Arg-Gly-Asp) which mediates virus binding to integrins and viral internalization via receptor-mediated endocytosis (Wickham et al. (1995) *Gene Therapy* 2:750-756).

The efficiency of cationic lipid transfections has been shown to be enhanced by the addition of whole virus particles to the transfection mixture. Certain viral components may also enhance the efficiency of cationic lipid-mediated transfection. For example, Kamata et al. ((1994) *Nucl. Acids Res.* 22:536) suggested that "Lipofectin™"-mediated transfections may be enhanced 3-4-fold by adding influenza virus hemagglutinin peptides to the transfection mixture. Antibodies have been shown to enhance cationic lipid transfections (Trubestsky, et al, (1992) *BBA* 1131, 311-313) and transferrin-poly lysine or asialoglycoprotein polylysine have been shown to enhance cationic lipid transfection (Mack et al, (1994) *Am J Med. Sci.* 138-143.

Nevertheless, these methods do not work for all cell types, require relatively complex protocols and are inconvenient. It is apparent, therefore, that new and improved methods for introducing macromolecules, and particularly nucleic acids, into cell, are greatly to be desired. In particular, improved methods for introducing nucleic acids into a wider variety of cells, and particularly into primary cells, are greatly to be desired.

SUMMARY OF THE INVENTION

Disclosed herein are compositions and methods that provide improved efficiency for introducing macromolecules, such as nucleic acids, into cells. Accordingly, provided herein is a complex containing a nucleic acid molecule, a transfection agent and a fusion agent, where the fusion agent contains a fusion-promoting amino acid sequence derived from a fusion protein of a non-enveloped virus. The non-enveloped virus may be a Reovirus, for example, Avian Reovirus, Nelson Bay Reovirus, or Pulau Reovirus. In certain aspects, the complexes contain a macromolecule to be introduced into the cell, such as a peptide, a protein, or a nucleic acid.

The fusion agent may contain a nucleic acid binding moiety functionally linked to the fusion promoting amino acid sequence. Suitable nucleic acid binding moieties include a polycationic peptide sequence, a polyamine, a peptide nucleic acid, spermine, spermidine, carboxyspermidine and the like. The nucleic acid binding moiety may be covalently linked to the fusion promoting amino acid sequence. The transfection agent may be a cationic lipid, such as those described below, a polyamine, a polycationic peptide sequence, or a cationic dendrimer or the like.

The fusion promoting amino acid sequence also may be functionally linked to a lipid, such as a cationic or neutral lipid, and the linked moiety may be used for delivery of macromolecules into cells. For example, a peptide containing the fusion promoting amino acid sequence may be covalently linked to a lipid, such as a cationic lipid, using methods that are well known in the art.

The complex may also contain a transfection enhancing agent, such as a nuclear localization protein or peptide, a fusogenic peptide or protein, receptor-ligand peptide or protein, a transport peptide or protein, or a second viral peptide or protein that is distinct from the fusion promoting amino acid sequence. The second viral peptide may be derived from a virus such as an influenza virus, a vesicular stomatitis virus, an adenovirus, an alphavirus, a Semliki Forest Virus, a hepatitis virus, a herpes virus, an HIV virus, or a simian virus. The transfection enhancing agent may also be, for example, insulin, a transferrin, a epidermal growth factor, a fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, an arginine rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, or fragments thereof. The transfection enhancing agent may be chloroquine, a lysosomotrophic compound or combinations thereof. The transfection agent may contain multimers of the same or different peptides or proteins.

In particular embodiments, the transfection agent contains at least one cationic lipid, and may optionally also contain one or more neutral lipids. The cationic lipid may contain at least one monovalent cationic lipid or polycationic lipid, for example, DOSPA, DOSPER, DOGS, TMTPS, TMTOS, TMTLS, TMTMS, TMDOS. N-1-dimethyl-N-1-(2,3-dia-oleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-β-hydroxyethylamine), L-Lysine-bis(O,O'-oleoyl-β-hydroxyethyl)amide dihydrochloride, L-Lysine-bis-(O,O'-palmitoyl-β-hydroxyethyl)amide dihydrochloride, 1,4-bis[(3-(3-aminopropyl)-alkylamino)-2-hydroxypropyl)piperazine, L-Lysine-bis-(O,O'-myristoyl-β-hydroxyethyl)amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis[(3-(3-aminopropyl)-oleylamino)-2-hydroxypropyl]piperazine, L-Ornithine-bis-(O,O'-palmitoyl-β-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperazine, L-Arginine-bis-(O,O'-oleoyl-β-hydroxyethyl)amide dihydrochloride, bis[(3-(3-aminopropyl)-myristylamino)-2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-β-hydroxyethyl)amide dihydrochloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethylammonium iodide, 1,4-bis[(3-myristylamino)propyl]piperazine, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N—(N',N'-dimethylaminoethane)carbamoyl]cholesterol, and 3β-[N-(polyethyleneimine)-carbamoyl]cholesterol, 1,4-bis[(3-palmitylamino)propyl] piperazine, L-Ornithylglycyl-N-(1-heptadecyloctadecyl) glycinamide, $N^2,N^5$-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl] piperazine $N^2$—[$N^2,N^5$-Bis(3-aminopropyl)-L-ornithyl]-N, N-dioctadecyl-L-glutamine, $N^2$—[$N^2,N^5$-Bis (aminopropyl)-L-ornithyl]-N—N-dioctadecyl-L-α-glutamine, 1,4-bis[(3-(3-amino-2-hydroxypropyl)-oleylamino)2-hydroxypropyl]piperazine, $N^2$—[$N^2,N^5$-Bis (aminopropyl)-L-ornithyl]-N—N-dioctadecyl-L-α-asparagine, N—[$N^2$—[$N^2,N^5$-Bis[(1,1-dimethylethoxy) carbonyl]-$N^2,N^5$-bis[3-[(1,1-dimethylethoxy)carbonyl] aminopropyl]-L-ornithyl-N—N-dioctadecyl-L-glutaminyl]-L-glutamic acid, $N^2$—[$N^2,N^5$-Bis(3-aminopropyl)-L-ornithyl]-N,N-dioleyl-L-glutamine, $N^2$—[$N^2,N^5$-Bis (aminopropyl)-L-ornithyl]-N—N-dioleyl-L-α-glutamine, 4-bis[(3-(3-amino-2-hydroxypropyl)-myristylamino)-2-hydroxypropyl]piperazine, $N^2$—[$N^2,N^5$-Bis(aminopropyl)-L-ornithyl]-N—N-dioleyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2,N^5$-Bis(3-aminopropyl)-L-ornithyl]-N,N-dipalmityl-L-glutamine, $N^2$—[$N^2,N^5$-Bis(aminopropyl)-L-ornithyl]-N—N-dipalmityl-L-α-glutamine, $N^2$—[$N^2,N^5$-Bis (aminopropyl)-L-ornithyl]-N—N-dipalmityl-L-α-asparagine, N—[$N^2$—[$N^2,N^5$-Bis[(1,1-dimethylethoxy)

carbonyl]-$N^2,N^5$-bis[3-[(1,1-dimethylethoxy)carbonyl]aminopropyl]-L-ornithyl-N—N-dipalmityl-L-glutaminyl]-L-glutamic acid, $N^2$—[$N^2,N^5$-Bis(3-aminopropyl)-L-ornithyl]-N,N-dimyristyl-L-glutamine, $N^2$—[$N^2,N^5$-Bis(aminopropyl)-L-ornithyl]-N—N-dimyristyl-L-α-glutamine, $N^2$—[$N^2,N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dimyristyl-L-glutaminyl]-L-glutamic acid, 1,4-bis[(3-(3-aminopropyl)-myristylamino)propyl]piperazine, $N^2$—[$N^2,N^5$-Bis(3-aminopropyl)-L-ornithyl]-N,N-dilaureyl-L-glutamine, $N^2$—[$N^2,N^5$-Bis(aminopropyl)-L-ornithyl]-N—N-dilaureyl-L-α-glutamine, $N^2$—[$N^2,N^5$-Bis(aminopropyl)-L-ornithyl]-N—N-dilaureyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dilaureyl-L-glutaminyl]-L-glutamic acid, 3-[N',N''-bis(2-tertbutyloxycarbonylaminoethyl)guanidino]-N,N-dioctadec-9-enylpropionamide, 3-[N',N''-bis(2-tertbutyloxycarbonylaminoethyl)guanidino]-N,N-dipalmitylpropionamide, 3-[N',N''-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydroxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)-)4-(3-amino-propylamino)-4-tetradecylcarbamoyl-butylcarbamic acid cholestryl ester, (3-Amino-propyl)-)4-(3-amino-propylamino-4-carbamoylbutylcarbamic acid cholestryl ester, (3-Amino-propyl)-4-(3-amino-propylamino)-4-(2-dimethylamino-ethylcarbamoy l)-butylcarbamic acid cholestryl ester, Spermine-5-carboxyglycine (N'-stearyl-N'-oleyl)amide tetratrifluoroacetic acid salt, Spermine-5-carboxyglycine (N'-stearyl-N'-elaidyl)amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis(3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-aminopropyl)-N,N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxyethyl)-piperazinium bromide, N-(3-aminopropyl)-N,N'-bis-(myristyloxyethyl)-piperazinium bromide, N-(3-aminopropyl)-N-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide. The neutral lipids may be, for example DOPE, DPhPE, or cholesterol.

In other embodiments the transfection agent may contain involves at least one polyamine transfection agent. Suitable polyamines include dense star dendrimers, PAMAM dendrimers, $NH_3$ core dendrimers, ethylenediamine core dendrimers, dendrimers of generation 5 or higher, dendrimers with substituted groups, dendrimers having one or more amino acids, grafted dendrimers, activated dendrimers, polyethylenimine, and polyethylenimine conjugates.

In specific embodiments, the fusion promoting amino acid sequence may be covalently linked to the transfection agents, the cationic lipid the neutral lipid, and/or the polyamine.

In other embodiments, the fusion promoting amino acid sequence may be conjugated to a nucleic acid binding group. The nucleic acid binding group may be linked to a polyamine or peptide nucleic acid. The polyamine may contain at least one spermine moiety.

A complex as described above may contain two transfection agents selected from the group consisting of fusogenic agents, nuclear localization sequences, transport peptides, receptor-ligand and a cell adhesion peptide.

The invention further provides pharmaceutical compositions, containing a complex as described above, and a pharmaceutical carrier.

The invention further provides methods of transfecting a cell, by contacting a cell with a complex as described above. The cell may be primary cell culture, a passaged cell culture or a cell line. Suitable cells include human cell lines and animal cell lines. The cell may be a fibroblast.

In one method, a nucleic acid is contacted with a fusion agent and the resulting mixture is added to a mixture of a cationic lipid and a neutral lipid, where the fusion agent contains a fusion-promoting amino acid sequence derived from a fusion protein of a non-enveloped virus.

In another method, a fusion agent is contacted with a transfection agent followed by addition of a nucleic acid or protein capable of aggregating the peptide- or protein-nucleic acid complex, where the fusion agent contains a fusion-promoting amino acid sequence derived from a fusion protein of a non-enveloped virus.

The invention further provides kits containing a transfection agent and a peptide or protein or a modified peptide or modified protein derived from a fusion promoting amino acid sequence of Avian Reovirus, Nelson Bay Reovirus, Pulau Reovirus or any Reovirus that may be capable of enhancing transfection of the transfection agent. The kit may also contain a cationic lipid transfection agent. The cationic lipid transfection agent may be selected from the group consisting of LipofectAmine™ 2000, LipofectAmine™, Lipofectin®, DMRIE-C, CellFectin® (Invitrogen), Oligofectamine® (Invitrogen), LipofectAce® (Invitrogen), Fugene® (Roche, Basel, Switzerland), Fugene® HD (Roche), Transfectam® (Tranfectam, Promega, Madison, Wis.), Tfx-10® (Promega), Tfx-20® (Promega), Tfx-50® (Promega), Transfectin™ (BioRad, Hercules, Calif.), SilentFect™ (Bio-Rad), Effectene® (Qiagen, Valencia, Calif.), DC-chol (Avanti Polar Lipids), GenePorter® (Gene Therapy Systems, San Diego, Calif.), DharmaFect 1® (Dharmacon, Lafayette, Colo.), DharmaFect 2® (Dharmacon), DharmaFect 3® (Dharmacon), DharmaFect 4® (Dharmacon), Escort™ III (Sigma, St. Louis, Mo.) and Escort™ IV (Sigma)) The kit may also contain a polycationic polymer transfection agent, and also may contain a diagnostic nucleic acid.

The present invention provides novel cationic lipids, and compositions that include such cationic lipids, that are useful for the delivery of macromolecules, such as nucleic acids, into cells. These novel cationic lipids have the structure according to Formula (I):

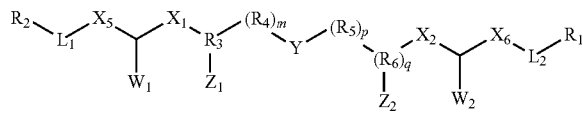

where $X_1$ and $X_2$ independently may be selected from the group consisting of $(CH_2)_n$, $(CHOH)_n$, and $CONH$; $X_5$ and $X_6$ independently are $(CH_2)_{1-6}$; $W_1$ and $W_2$ independently may be selected from the group consisting of hydrogen, —OH, —O—$(C_1$-$C_{30})$alkyl, —O—$(C_1$-$C_{30})$ alkenyl, —O—$(C_1$-$C_{30})$alkynyl, —$NH_2$, —$NH(CH_2)_sCH_3$, —$N((CH_2)_sCH_3)$, —SH, and —NH—$NH_2$; $R_3$ and $(R_6)_q$ independently may be selected from the group consisting of N, NH, CH, $N(CH_2)_sCH_3$, $(CH)_n$, $(COH)_n$, CON— and q=0-1; $R_4$ and $R_5$ independently may be selected from the group consisting of $(CH_2)_n$, $(CH_2$—CHOH—$CH_2)_n$, $(CHOH)_n$, HNCO, CONH, CO, —O—, —S—, —S—S—, polyamide and an ester linkage; $L_1$ and $L_2$ independently may be selected from the group consisting of —NH—, —O—, —NHCO—, —CONH—, —OCO—, —COO—, —CO—, —S—, —S—S—, —NHC(O)O—, —OC(O)NH—, —NHCONH—, —NHC(=NH)NH—, —S(O)— and —$SO_2$—; Y is a heterocyclic moiety containing at least one amine or amide moiety, where the points of attachment of Y are carbon and/or heteroatoms. Examples of suitable heterocyclic moieties include, but are not limited to, piperazine, piperidine, pyridine, pyrrolidine, and imidazole moieties and derivatives thereof. In specific embodiments, the heterocyclic moiety is a piperazine ring, where the points of attachment optionally are at one or both of the nitrogen atoms. The heterocyclic moiety may optionally be substituted with up to 4 substituents independently selected from the group consisting of OH, =O, a carboxylic acid, an ether, a polyether, an alkylaryl, an amino alcohol, an amide, an straight chain alkyl, branched alkyl, cycloalkyl, straight chain alkenyl, branched alkenyl, cycloalkenyl, straight chain alkynyl, branched alkynyl, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine, amino alcohol, alcohol, ether, polyether, aryl, benzyl, heterocycle, cycloalkyl, alkyl polyamine, alkenyl polyamine, alkynyl polyamine, spermidine, spermine, carboxy spermine, guanidinium, pyridinium, pyrollidinium, piperidinium, piperazinium, and amino acyl, where the alkyl, alkenyl, alkynyl and alkylamine groups are optionally substituted with at least one hydroxyl, or at least one amine, or at least one hydroxyl and at least one amine; $R_1$ and $R_2$ independently may be selected from the group consisting of hydrogen, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine amino alcohol, alkyl polyamine, alkenyl polyamine, alkynyl polyamine, spermidine, spermine, carboxy spermine, guanidinium, pyridinium, pyrollidinium, piperidinium, piperazinium, amino acyl, peptidyl, and protein; $Z_1$ and $Z_2$ independently may be selected from the group consisting of straight chain alkyl, branched alkyl, cycloalkyl, straight chain alkenyl, branched alkenyl, cycloalkenyl, straight chain alkynyl, and branched alkynyl, m, n, p, and s independently are 0-6, with the proviso that when m, n, and p all are 0 then Y is eliminated and $R_3$ is bonded directly to $X_2$. In one embodiment, $L_1$ and $L_2$ independently may be selected from the group consisting of —NH—, —O—, —NHCO—, —CONH—, —NHC(O)O—, —OC(O)NH—, —NHCONH—, —NHC(=NH)NH—, —S(O)— and —$SO_2$—, and in another embodiment, $L_1$ and $L_2$ independently may be selected from the group consisting of —NH—, —NHCO—, —CONH—, —NHC(O)O—, and —OC(O)NH—.

In accordance with one aspect of the invention, there is provided a lipid having the structure according to Formula (II)

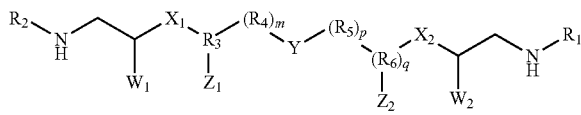

where $X_1$, $X_2$, $W_1$, $W_2$, $R_3$, $(R_6)$, $R_4$, $R_5$, Y, $R_1$, $R_2$, $Z_1$, $Z_2$ m, n, p, and s are as defined above.

In a particular embodiment, Y may be

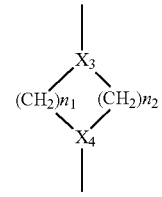

where $X_3$ and $X_4$ are independently selected from N and CH and where $n_1$ and $n_2$ independently are 1-10. In any of the above embodiments, $X_3$ and $X_4$ are N and $n_1$ and $n_2$ independently are 1-10. For example, $n_1$ and $n_2$ may be both 2. This cyclic structure may optionally be substituted with up to 4 substituents as defined above for Y.

In accordance with another aspect of the invention there is provided a composition containing a lipid of Formula (I) and a co-lipid that is neutral, positively charged (such as a cationic lipid) or negatively charged. The co-lipid may be, for example, DOPE or cholesterol. The cationic lipid may include, but is not limited to, LipofectAmine™ 2000, LipofectAmine™, Lipofectin®, DMRIE-C, CellFectin®, Oligofectamine®, LipofectAce®, (Invitrogen) Fugene®, Fugene® HD (Roche), Transfectam®, Tfx-10®, Tfx-20, ®Tfx-50® (Promega), Transfectin™, SilentFect™ (Bio-Rad), Effectene® (Qiagen), or DC-chol (Avanti Polar Lipids), GenePorter® (GTS), DharmaFect 1®, DharmaFect 2®, DharmaFect 3®, DharmaFect 4® (Dharmacon) Escort™ III or Escort™ IV (Sigma) The composition may further contain a macromolecule, including, but not limited to, a nucleic acid. Such nucleic acids can include, for example, DNA or RNA, either single stranded or double stranded (e.g. ssDNA, ssRNA, dsDNA, and dsRNA), and can include naturally occurring or non-naturally-occurring bases. The nucleic acid may be a plasmid, which may encode an RNA molecule that is self complementary and that forms a region of double stranded RNA. The nucleic acid may be an siRNA. Any of these compositions may further contain a eukaryotic cell, such as, by way of example only, a mammalian cell.

In accordance with yet another aspect of the invention there is provided a method of introducing a macromolecule into a cell, comprising contacting a eukaryotic cell with a composition as described above.

In accordance with another aspect of the invention there is provided a composition comprising a lipid of Formula (I) as described herein, or a composition comprising a lipid of Formula (I) and a co-lipid as described above, and a peptide or protein. The peptide or protein may be a transfection enhancing peptide or protein that functions for nuclear or other sub-cellular localization, transport or trafficking. The peptide or protein may be transfection enhancing peptides or proteins that function as receptor ligands, that comprises a cell-adhesion signal, a cell-targeting signal, a cell-internalization signal or an endocytosis signal, and combinations thereof. The peptide or protein may be selected from the group consisting of peptides and proteins derived from enveloped and non enveloped viruses, bacteria, insulin, a transferrin, an epidermal growth factor, a fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a fusogenic peptide or protein, a reovirus fusion protein, a histone protein, an arginine-rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a adapatin protein, a bacteriacidal-permability-increasing protein, a nisin, a buforin, and fragments thereof. These compositions may further contain a macromolecule, such as a nucleic acid, which may be a DNA molecule such as a double stranded DNA molecule, optionally in the form of a plasmid. The plasmid may encode an RNA molecule that is self complementary and that forms a region of double stranded RNA. The nucleic acid may comprise an RNA molecule, such as a double stranded RNA molecule, for example an siRNA. These compositions may be used to introduce a macromolecule, a peptide or a protein into a cell, by contacting a eukaryotic cell with a composition as described above. The peptide or protein may be a transfection enhancing peptide or protein that functions for nuclear or other sub-cellular localization, transport or trafficking, is a receptor ligand, that comprises a cell-adhesion signal, a cell-targeting signal, a cell-internalization signal or an endocytosis signal, and combinations thereof that is covalently modified with spermine, spermidine or polylysine.

In accordance with another aspect of the invention there is provided a method of introducing a desired molecule into a tissue, comprising contacting said tissue with a composition containing the desired molecule and a lipid or composition as described above. The desired molecule may be, for example, a nucleic acid, a peptide, or a protein.

In accordance with yet another aspect of the invention there is provided a kit for transfecting a cell, comprising a lipid of Formula (I).

In another aspect, the invention also provides complexes as described above where Y is

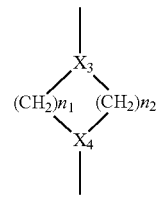

where $X_3$, $X_4$, $n_1$ and $n_2$ are as defined above. In these complexes, the cationic lipid may be a 1,4-bis[(3-(3-aminopropyl)-alkylamino)propyl)piperazine lipid. In the complexes described above, the fusion promoting amino acid sequence may be a peptide comprising 10-30 contiguous amino acids of a sequence selected from the group consisting of:

```
                                          (SEQ ID NO: 1)
MLRMPPGSCNGATAVFGNVHCQAAQNTAGGDLQATSSIIA, (SEQ ID NO: 2)
MPRMPPGSCNGATAVFGNVHCQAAQNTAGGDLQATSSIIA, (SEQ ID NO: 3)
MSGDCAGLVSVFGSVHCQSSKNKAGGDLQATSILTTYWPH, (SEQ ID NO: 4)
MSSDCAKIVSVFGSVHCQSSKNSAGGDLQATSVFTTYWPH, (SEQ ID NO: 5)
MGQRHSIVQPPAPPPNAFVEIVSSSTGIIIAVGIFAFIFS,
and (SEQ ID NO: 6)
MGSGPSNFVNHAPGEAIVTGLEKGADKVAGTISHTIWEVI.
```

The peptide may contain at least 10 contiguous amino acids of an amino acid sequence selected from the group consisting of:

```
                                          (SEQ ID NO: 7)
            RMPPGSCNGATAVFGNVH, (SEQ ID NO: 8)
            GDCAGLVSVFGSVH, (SEQ ID NO: 9)
            SDCAKIVSVFGSVH, (SEQ ID NO: 10)
            QRHSIVQPPAPPPNAFVEIVS,
            and (SEQ ID NO: 11)
            SGPSNFVNHAPGEAIVT.
``` covalently linked to between 8 and 30 lysine residues.

In the kits described above, a nucleic acid binding moiety and a peptide or protein or the modified peptide or modified protein derived from the fusion promoting amino acid sequence of a Reovirus, may be in the same container. A nucleic acid binding moiety, a catioinic lipid transfecting agent, and a peptide or protein or a modified peptide or modified protein derived from a fusion promoting amino acid sequence of a Reovirus may be in the same container. The kits may also contain a transfection enhancing reagent. In one embodiment a kit contains a nucleic acid binding moiety, a transfection enhancing reagent, a cationic lipid transfecting agent, and a peptide or protein or a modified peptide or modified protein derived from a fusion promoting amino acid sequence of a Reovirus may be in the same container.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
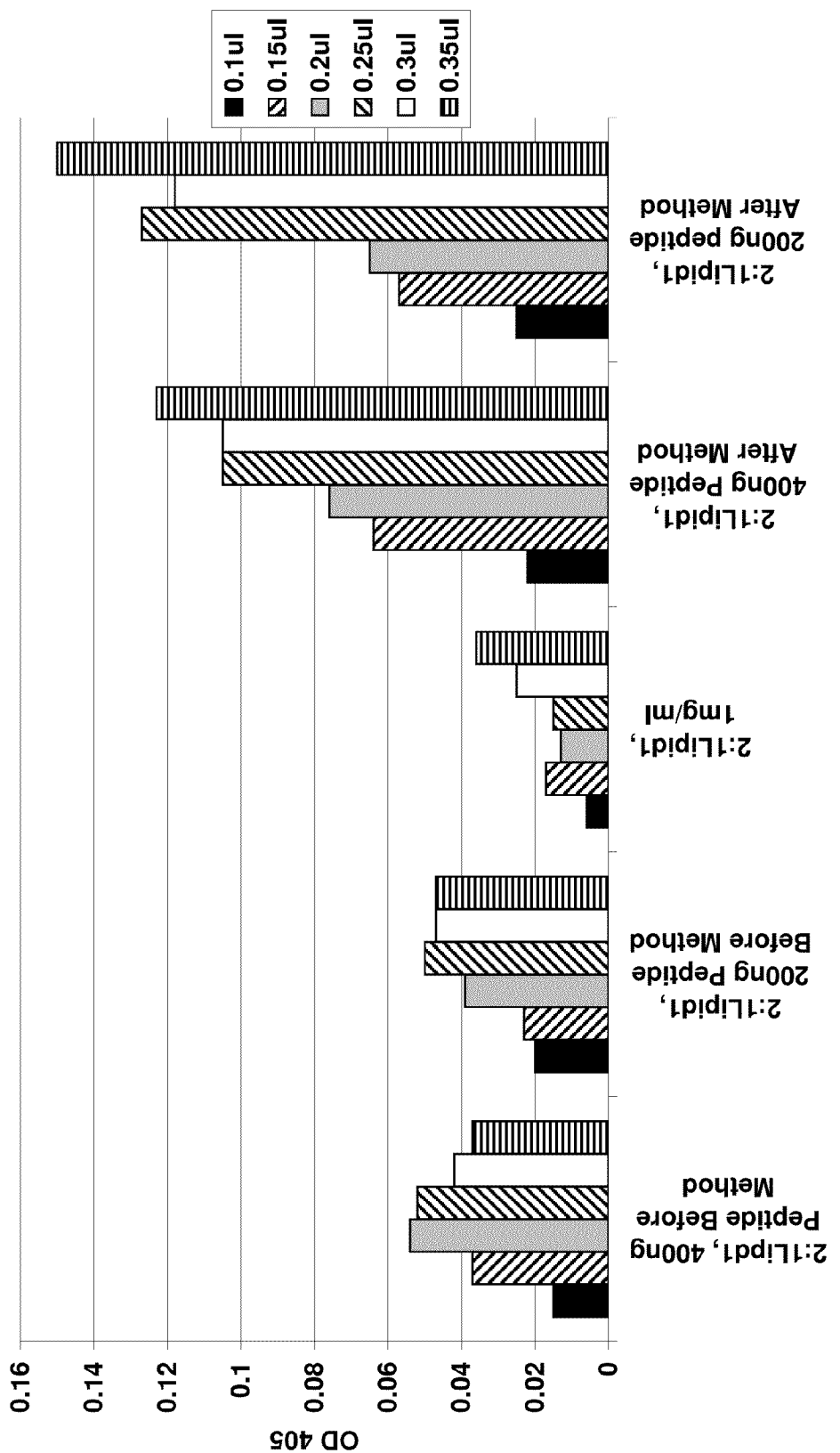
FIG. 1 shows the results of transfection of CHO-K1 cells using the complexes of the invention using "before" and "after" protocols.

Compositions and methods for improved delivery of macromolecules into eukaryotic cells are provided. The compositions and methods are effective in a wide variety of cells, and provide a high efficiency of transfection. Specifically, it has been found that fusogenic peptides from fusion proteins of non-enveloped viruses can dramatically enhance the efficiency of transfection of eukaryotic cells mediated by transfection agents such as cationic lipids, polycationic polymers such as PEI and dendrimers. These fusogenic peptides are used as part of a transfection complex that efficiently delivers a macromolecule, for example, a nucleic acid, into a eukaryotic cell.

Novel cationic lipids and compositions of cationic lipids also are provided that are effective for the introduction of macromolecules such as nucleic acids, proteins and peptides into a variety of cells and tissues. The lipids can be used alone or in combination with other lipids such as DOPE or cholesterol to form liposomes or lipid aggregates that are highly effective for delivery of macromolecules into cells in vitro or in vivo. The lipids can also be used, for example, in combination with fusogenic peptides to prepare transfection complexes as described herein. Methods for delivering macromolecules into target cells and tissues using the lipids, alone or in combination, also are provided.

The lipids have the following general structure (Formula I):

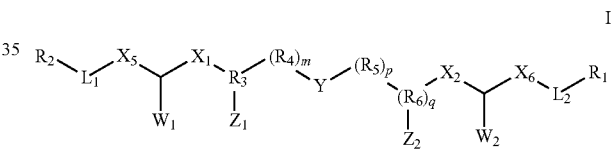

The skilled artisan will recognize that, although the molecules of the invention are shown here for convenience in their neutral (unprotonated) forms, these molecules will exist in a partially or fully protonated form in solutions of appropriate pH, and that the present invention encompasses the molecules in all their protonated, unprotonated, ionized and non-ionized forms without limitation, unless specifically indicated otherwise.

In compounds of Formula I, $X_1$ and $X_2$ may independently be selected from the group consisting of $(CH_2)_n$, $(CHOH)_n$, and CONH. $X_5$ and $X_6$ independently may be $(CH_2)_{1-6}$. $W_1$ and $W_2$ independently may be selected from the group consisting of, hydrogen, —OH, —O—$(C_1$-$C_{30})$alkyl, —O—$(C_1$-$C_{30})$alkenyl, —O—$(C_1$-$C_{30})$alkynyl, —NH$_2$, —NH$(CH_2)_s$CH$_3$, —N$((CH_2)_s$CH$_3)$, —SH, and —NH—NH$_2$. $R_3$ and $R_6$ independently may be selected from the group consisting of N, NH, CH, N$(CH_2)_s$CH$_3$, $(CH)_n$, $(COH)_n$, CON— and q=0-1. $R_4$ and $R_5$ independently may be selected from the group consisting of $(CH_2)_n$, $(CH_2$—CHOH—CH$_2)_n$, $(CHOH)_n$, HNCO, CONH, CO, —O—, —S—, —S—S—, polyamide and an ester linkage. $L_1$ and $L_2$ independently may be selected from the group consisting of —NH—, —O—, —NHCO—, —CONH—, —OCO—, —COO—, —CO—, —S—, —S—S—, —NHC(O)O—, —OC(O)NH—, —NH-CONH—, —NHC(=NH)NH—, —S(O)— and —SO$_2$—.

Y is a heterocyclic moiety containing at least one amine or amide moiety. The points of attachment of Y may be carbon and/or heteroatoms. Examples of suitable heterocyclic moieties include, but are not limited to, piperazine, piperidine, pyridine, pyrrolidine, and imidazole moieties and derivatives thereof. In specific embodiments, the heterocyclic moiety is a piperazine ring, where the points of attachment optionally are at one or both of the nitrogen atoms. The heterocyclic moiety may optionally be substituted with up to 4 substituents independently selected from the group consisting of OH, =O, a carboxylic acid, an ether, a polyether, an alkylaryl, an amino alcohol, an amide, an straight chain alkyl, branched alkyl, cycloalkyl, straight chain alkenyl, branched alkenyl, cycloalkenyl, straight chain alkynyl, branched alkynyl, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine, amino alcohol, alcohol, ether, polyether, aryl, benzyl, heterocycle, cycloalkyl, alkyl polyamine, alkenyl polyamine, alkynyl polyamine, spermidine, spermine, carboxy spermine, guanidinium, pyridinium, pyrollidinium, piperidinium, piperazinium, and amino acyl, where the alkyl, alkenyl, alkynyl and alkylamine groups are optionally substituted with at least one hydroxyl, or at least one amine, or at least one hydroxyl and at least one amine, $R_1$ and $R_2$ independently may be selected from the group consisting of hydrogen, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine amino alcohol, alkyl polyamine, alkenyl polyamine, alkynyl polyamine, spermidine, spermine, carboxy spermine, guanidinium, pyridinium, pyrollidinium, piperidinium, piperazinium, amino acyl, peptidyl, and protein. In the context of the present invention it will be understood that, unless specifically indicated otherwise, an alkylamine can be an amine containing a short or a long alkyl chain. Similarly, an alkenylamine will be understood to contain a short or long alkenyl chain, and the same is true for alkynylamines.

$Z_1$ and $Z_2$ independently may be selected from the group consisting of straight chain alkyl, branched alkyl, cycloalkyl, straight chain alkenyl, branched alkenyl, cycloalkenyl, straight chain alkynyl, branched alkynyl where m, n, p, and s independently are 0-6, with the proviso that when m, n, and p all are 0 then Y is eliminated and $R_3$ is bonded directly to $X_2$.

Y may have the following cyclic structure

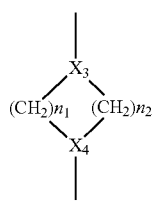

where $X_3$ and $X_4$ may independently be selected from N and CH and $n_1$ and $n_2$ independently are 1-10. Typically, Y is a 6-9 membered ring and, in exemplary specific embodiments, $X_3$ and $X_4$ are both N and $n_1$ and $n_2$ are both 2, i.e. Y is an optionally substituted piperazine moiety. This structure may optionally be substituted with 1-4 moieties as described above for Y.

In other specific embodiments Y can have the following cyclic structure:

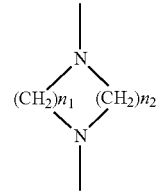

where $n_1$, and $n_2$ independently are 1-10. Typically $n_1+n_2$ is 3-7. Such a cyclic structure may optionally be substituted with 1-4 moieties independently selected as described above for Y.

Examples of the lipids may be defined by the following structure, where $L_1$ and $L_2$ both are NH and $X_5$ and $X_6$ are $CH_2$:

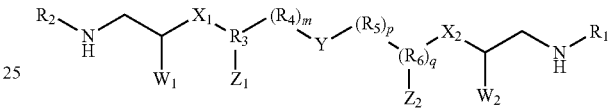

In this structure $R_1$-$R_6$, $W_1$, $W_2$, $X_1$, $X_2$, $Z_1$, $Z_2$, Y m, p, and q are as defined above.

A specific example of the lipids of the invention covered by the above formula is compound 5 given in example 1 below where $R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=oleoyl; $W_1$, $W_2$=H; q, p, m=1; and Y=piperazine. Other specific examples include, but are not limited to, the following:

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=palmityl; $W_1$, $W_2$=H; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=myristyl; $W_1$, $W_2$=H; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=lauryl; $W_1$, $W_2$=H; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=stearyl; $W_1$, $W_2$=H; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=oleoyl; $W_1$, $W_2$=OH; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=palmityl; $W_1$, $W_2$=OH; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=myristyl; $W_1$, $W_2$=OH; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=lauryl; $W_1$, $W_2$=OH; q, p, m=1; and Y=piperazine;

$R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=stearyl; $W_1$, $W_2$=OH; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=oleoyl; $W_1$, $W_2$=H; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=palmityl; $W_1$, $W_2$=H; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=myristyl; $W_1$, $W_2$=H; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=lauryl; $W_1$, $W_2$=H; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=stearyl; $W_1$, $W_2$=H; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=oleoyl; $W_1$, $W_2$=OH; q, p, m=1; and Y=piperazine:

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=palmityl; $W_1$, $W_2$=OH; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=myristyl; $W_1$, $W_2$=OH; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=lauryl; $W_1$, $W_2$=OH; q, p, m=1; and Y=piperazine;

$R_1$, $R_2$=H; $X_1$, $X_2$=$CH_2$; $R_4$, $R_5$=$CH_2$—$CH_2$—$CH_2$; $R_3$, $R_6$=N; $Z_1$, $Z_2$=stearyl; $W_1$, $W_2$=OH; q, p, m=1; and Y=piperazine.

The skilled artisan will recognize that the cationic lipids of the present invention are not limited to these specific examples.

In the context of the present invention, a short chain alkyl group is typically, unless otherwise defined, $C_1$-$C_6$ alkyl. A long chain alkyl group is typically, unless otherwise defined, $C_{10}$-$C_{20}$ alkyl, or $C_{10}$-$C_{30}$ alkyl. When not specifically defined, either definition may be used, as appropriate. The skilled artisan also will appreciate that other derivative groups containing alkyl moieties, for example, alkoxy moieties and the like, also may contain short and/or long chain groups as appropriate in the context, unless otherwise defined. An alkenyl group contains at least one cis or trans carbon-carbon double bond and typically is $C_{10}$-$C_{30}$ in chain length. Exemplary alkenyl groups contain one or two cis double bonds where the double bonds are disubstituted. An alkynyl group contains at least one carbon-carbon triple bond and typically is $C_{10}$-$C_{30}$ in chain length. The alkyl, alkenyl or alkynyl groups may be straight chain or branched. The skilled artisan also will appreciate that other derivative groups containing alkyl moieties, for example, alkoxy moieties and the like, also may contain short and/or long chain groups as appropriate in the context, unless otherwise defined.

Lipids of the invention may be prepared by methods that are well known in the art. See, for example, U.S. Pat. Nos. 5,334,761, 5,264,618, 5,744,335, 5,527,928, WO00/27795 and Benerjee et al. (*J. Med. Chem.*, 44, 4176 (2001), each of which is hereby incorporated by reference in its entirety.

Transfection Complexes

In one embodiment, a transfection complex provided herein contains the macromolecule that is to be delivered to the cell, a fusogenic peptide, and a transfection agent. The complex is formed and then added to the cells to be transfected. In other embodiments, where the macromolecule is a nucleic acid, the fusogenic peptide is functionally linked to a nucleic acid binding moiety. For example, the fusogenic peptide can be linked to a peptide sequence that binds nucleic acid, or to another polycationic nucleic acid binding moiety as describe in more detail below. The functional linkage may be a covalent linkage or may be non-covalent. An example of a non-covalent linkage between the peptide and the nucleic acid binding moiety is where the peptide contains a first member of a binding pair, and the nucleic acid binding moiety contains a second member of the binding pair, where association of the first and second members of the binding pair results in functional linkage of the fusogenic peptide and the nucleic acid binding moiety. Suitable binding pairs include an antibody and an antigen, streptavidin/biotin, and the like. In certain illustrative aspects, transfection complexes are formed using complexes that include a fusogenic peptide as disclosed herein, and a transfection reagent. These complexes that include a fusogenic peptide and a transfection reagent form another embodiment of the invention.

In still other embodiments, the complex may also contain a transfection enhancing agent that facilitates entry of the complex into the target cell or that facilitates subcellular or cellular targeting of the complex. Exemplary transfection enhancing agents include nuclear localization peptides, another fusogenic peptide or protein, a ligand for a cell-surface receptor, and the like, as described in more detail below.

In other embodiments, the transfection complex of the invention contains the macromolecule that is to be delivered to the cell and a fusogenic peptide. Furthermore, in additional embodiments, provided herein is a transfection complex that includes a transfection agent and a fusogenic peptide. Any of the transfection complexes provided herein can include a transfection enhancing agent, such as a nuclear localization sequence. Furthermore, the transfection complexes provided herein can include a nucleic acid binding group.

Fusogenic peptides are provided that enhance transfection efficiency of macromolecules into cells. The peptides have amino acid sequences that are derived from fusion proteins of non enveloped Reoviruses. Although the skilled artisan will recognize that proteins, fragment thereof, or modified peptides, proteins and fragments derived from fusion proteins of a variety of non-enveloped viruses may be used in the present invention, it has been found that peptides from Avian Reovirus, Nelson Bay Reovirus, and Pulau Reovirus are particularly useful. The compositions and methods of the invention, in illustrative embodiments, comprise peptides, proteins and fragments thereof, modified peptides, modified proteins and modified fragments thereof, peptide conjugates, protein conjugates and conjugates of fragments thereof, from such non-enveloped viruses.

These peptides are complexed with a transfection agent and a macromolecule, and the resulting complex is added to cells in culture, resulting in efficient intracellular delivery of the macromolecule. The complexes and methods of the invention my be used to deliver a wide variety of macromolecules into cells but are particularly useful for the delivery of nucleic acids. It will be understood that references to delivery of nucleic acid in the context of the present invention will also convey to the skilled artisan that other macromolecules generally also can be used in place of the nucleic acid.

In other embodiments, other peptides, proteins, fragment thereof, or modified peptides, proteins and fragments thereof that promote still more efficient transfection are used along with the complexes of the invention. In one embodiment these peptides, proteins or fragments thereof are bound or added to the nucleic acid prior to adding the complex, while in other embodiments the peptides, proteins, or fragments thereof may be added or complexed with the complex prior to addition of the nucleic acid. Alternatively, the nucleic acid may be combined with the complex prior to addition of the peptide, protein, etc.

Fusogenic Peptides

The present inventors have surprisingly found that amino acid sequences derived from non-enveloped viruses are highly efficient at promoting transfection of macromolecules into cells, including into cells such as primary cells, that are otherwise refractory to common transfection agents. Advantageously, the peptides have sequences that are derived from the N-terminal regions of fusion-associated small transmembrane (FAST) proteins encoded by non-enveloped fusogenic reoviruses.

These reoviruses enter cells by membrane fusion followed by syncytium formation. It is thought that syncytium formation is mediated by small non-structural transmembrane proteins, sometimes referred to as FAST proteins, that localize to the surface of the target cell and induce efficient cell-cell fusion. Shmulevitz et al., *EMBO J.* 19:902 (2000); Cheng et al., *J. Virol.*, 79:1853 (2005). Surprisingly, the present inventors have found that short peptides derived from these fusogenic proteins efficiently promote transfection of artificial complexes containing nucleic acids into cells.

Certain peptides derived from these fusogenic proteins are believed to be fusogenic peptides that provide illustrative examples of fusion promoting amino acid sequences according to the present invention. A fusogenic peptide included in the compositions and methods provided herein, can be derived from any fusogenic protein of a non-enveloped virus. Advantageously, the peptide comprises an amino acid sequence derived from the N-terminus of the fusogenic protein. Typically the peptide is derived from approximately the first 50 amino acids of the native fusogenic protein sequence, and advantageously contains 15-25 amino acids derived from the N-terminus of the fusogenic protein, although longer or shorter sequences also can be used. Isolated fusogenic peptides of Reoviruses provided herein, themselves form a separate embodiment of the invention.

Reovirus FAST proteins typically contain a conserved N-terminal domain structure comprising, in N-terminal to C-terminal order, a hydrophobic region, a transmembrane region and a polybasic region. In some viruses the hydrophobic region contains or is replaced by a polyproline motif. The N-terminus is optionally myristoylated. The peptides that are useful for the present invention typically are derived from the hydrophobic region prior to the transmembrane domain, although part or all of the transmembrane domain may be included in the sequence. Methods of identifying transmembrane domains are well known in the art. See, for example, White, *Annu. Rev. Physiol.*, 52:675-697 (1990). A typical transmembrane domain is a contiguous sequence of amino acids averaging 29 residues, with average hydrophobicity of 0.7±0.09 and an alanine+glycine content of 16%±8%.

The peptide can be myristoylated at the N-terminus although this is not required for efficient transfection. This is surprising because it has been reported that the presence of a fatty acid moiety is essential for membrane fusion in avian reovirus and Nelson Bay reovirus. Shmulevitz et al., *J. Virol.* 77:9769 (2003). The fusion promoting amino acid sequence also may be functionally linked to a lipid, such as a cationic or neutral lipid, and the linked moiety may be used for delivery of macromolecules into cells. For example, a peptide containing the fusion promoting amino acid sequence may be covalently linked to a lipid, such as a cationic lipid, using methods that are well known in the art.

It has also been described that reovirus FAST proteins contain a conserved region between the hydrophobic region and the transmembrane domain. See Shmulevitz et al., *J. Virol.* 77:9769 (2003). The peptides that are useful in the context of the present invention optionally may include amino acids from this conserved region; however, in the examples provided below, the peptides lack these amino acids.

The Nelson Bay Reovirus FAST fusogenic protein has the following sequence:

```
                                                  (SEQ ID NO: 12)
 1   MSSDCAKIVS VFGSVHCQSS KNSAGGDLQA TSVFTTYWPH FAIGGGIIVV

51   ILLLGLFYCC YLKWKTSQVK HTYRRELIAL TRSHVHSTPS GISYV
```

The complete sequence of the Avian reovirus FAST fusogenic protein is:

```
                                                  (SEQ ID NO: 13)
     MLRMPPGSCN GATAI/VFGNVH CQAAQNTAGG DLQATSSIIA

YWPYLAAGGG FLLIVIIFAI LYCCKAKVKA DAARSVFHRE

LVALSSGKHN AMAPPYNV
```

Prototypical peptides that are useful in the context of the present invention that are derived from this protein have the sequences provided below in the section entitled Protypical Avian reovirus fusogenic peptides.

The skilled artisan will recognize that other peptides can be derived from the fusion protein sequence that can be used in the present invention. In particular, peptides containing conservative amino acid substitutions may be used. Conservative amino acid substitutions are well known in the art. Typical substitutions can be made where the amino acids are similar in size and/or charge properties. For example, lysine and arginine, aspartate and glutamate and isoleucine and valine are pairs of similar amino acids. Methods of determining similarity between amino acid pairs have been described using a number of methods. For example, Dayhoff et al. (1978) in Atlas of Protein Sequence and Structure, Volume 5, Supplement 3, Chapter 22, pages 345-352, which is incorporated by reference herein, provides frequency tables for amino acid substitutions which can be employed as a measure of amino acid similarity. In addition, since the peptides are most conveniently produced by chemical peptide synthesis, non-naturally occurring amino acids can be substituted using known substitution patterns. For example, 2-amino-5-hexanoic acid can be used in place of methionine.

The present invention also includes peptides having defined sequence identities with the N-terminal region of reovirus fusogenic proteins. In particular, these peptides in illustrative embodiments, contain no more than about 25 contiguous amino acids of the N-terminal region sequence of a reovirus fusogenic protein, prior to the reovirus protein conserved region and the transmembrane domain. The peptides typically contain a sequence that is derived at least in part from the N-terminal hydrophobic domain of the fusogenic peptide sequence. The diagram below shows the approximate location of the hydrophobic (bold), conserved (underlined) and transmembrane (double underlined) domains for avian reovirus:

```
                                               (SEQ ID NO: 14)
MLRMPPGSCNGATAIFGNVHCQAAQNTAGG DLQATSSIIAYWPYLAAGGG

FLLIVIIFAILYCCKAKVKA DAARSVFHRE LVALSSGKHN

AMAPPYNV
```

The skilled artisan will recognize that in certain embodiments, peptides can be used that are at least 5, 10, 11, 12, 13, 14, 15, 16, 17, 18, 19, and 20 amino acids, and no more than 75, 70, 60, 50, 40, 30, or 25 amino acids in length having a region of greater than or equal to 50%, 60%, 70%, 75%, 80%, 85%, 90%, 95%, 99%, or 100% sequence identity with 5, 6, 7, 8, 9, 10, 11, 12, 13, 14, 15, 16, 17, 18, 19, 20, 25, 30, 40, 45, 50 or all amino acids of the amino terminal 50 amino acids of a Reovirus fusogenic FAST protein, for example an avian Reovirus fusogenic FAST protein or peptide derived therefrom, such as from an avian reovirus peptide having the sequence RMPPGSCN GATAIFGNVH (SEQ ID NO: 15). In another embodiment of the present invention, a fusogenic peptide of a fusion agent, has a sequence that is between 5 and 50 amino acids in length and includes at least 5, 6, 7, 8, 9, 10, 11, 12, 13, or 14 amino acids of a hydrophobic region of a Reovirus FAST protein and can optionally include all or a portion of the conserved region between the hydrophobic region and the transmembrane domain. Sequence identity can be calculated using, for example, sequence analysis software such as the Sequence Analysis Software Package of the Genetics Computer Group, University of Wisconsin Biotechnology Center, 1710 University Avenue, Madison, Wis. 53705. For example, amino acid sequences may be aligned to maximize identity using, if necessary, gaps to produce appropriate alignment. The percentage identity is calculated by recording all of the positions in which the amino acids of both sequences are identical, relative to the total number of positions.

The Nelson Bay Reovirus fusion protein, from which fusogenic peptides of the present invention can be derived, has the following sequence

```
                                               (SEQ ID NO: 12)
 1   MSSDCAKIVS VFGSVHCQSS KNSAGGDLQA TSVFTTYWPH FAIGGGIIVV

51   ILLLGLFYCC YLKWKTSQVK HTYRRELIAL TRSHVHSTPS GISYV
```

The hydrophobic region of the protein is shown in bold. Peptides derived from the first 1-50, advantageously the first 1-40, more advantageously the first 1-25 amino acids of this protein, can be used in the present invention. In an alternative embodiment, peptides that are 5 to 50 amino acids in length that include at least 5, 6, 7, 8, 9, 10, 11, 12, 13, or all amino acids of the hydrophobic region of a Reovirus are used. In another embodiment Advantageously, the peptides contain most or all of the hydrophobic region of the protein as shown above. Similarly, N-terminal peptides derived from the baboon reovirus or the reptilian reovirus can be used. See Corcoran et al., *J. Virol.*, 78:4342 (2004), and Dawe et al. *J. Virol.*, 76:2131 (2002), the contents of each of which are hereby incorporated by reference in their entireties. Peptides derived from the N-terminal region of the fusogenic peptides from other reoviruses, whether presently known or discovered in the future, can be used in the present invention. Specific further examples include peptides derived from the fusogenic protein of the Muscovy duck reovirus.

In certain embodiments, the fusogenic peptide of the present invention is 5 to 50 amino acids in length, preferably 10 to 40 amino acids in length, and includes at least 5, 6, 7, 8, 9, 10, 11, 12, 13, or 14 contiguous amino acids that are at least 80, 85, 90, 95, 99, or 100% identical to at least 5, 6, 7, 8, 9, 10, 11, 12, 13, or 14 amino acids of the hydrophobic region of a Reovirus FAST protein, in illustrative examples an Avian Reovirus FAST protein. The fusogenic peptide in certain illustrative examples includes a polycationic peptide sequence.

Prototypical Avian Reovirus Fusogenic Peptides

The specific examples of this section provide Prototypical Avian reovirus fusogenic peptides of the present invention.

Specific examples of peptides according to the invention include, but are not limited to, peptides that are 5-50 amino acids in length and that contain 5-30 contiguous amino acids from one of the following sequences:

```
                                                (SEQ ID NO: 1)
MLRMPPGSCNGATAVFGNVHCQAAQNTAGGDLQATSSIIA, (SEQ ID NO: 16)
MLRMPPGSCNGATAIFGNVHCQAAQNTAGGDLQATSSIIA, (SEQ ID NO: 2)
MPRMPPGSCNGATAVFGNVHCQAAQNTAGGDLQATSSIIA, (SEQ ID NO: 3)
MSGDCAGLVSVFGSVHCQSSKNKAGGDLQATSILTTYWPH, (SEQ ID NO: 4)
MSSDCAKIVSVFGSVHCQSSKNSAGGDLQATSVFTTYWPH, (SEQ ID NO: 6)
MGSGPSNFVNHAPGEAIVTGLEKGADKVAGTISHTIWEVI, (SEQ ID NO: 5)
MGQRHSIVQPPAPPPNAFVEIVSSSTGIIIAVGIFAFIFS, (SEQ ID NO: 6)
MGSGPSNFVNHAPGEAIVTGLEKGADKVAGTISHTIWEVI.
```

Further specific examples of peptides according to the invention include, but are not limited to, peptides that contain at least 5 contiguous amino acids from one of the following sequences:

```
                                               (SEQ ID NO: 17)
RMPPGSCNGATAVFGNVHCQAAQNTAGGDLQATSSIIA, (SEQ ID NO: 18)
RMPPGSCNGATAIFGNVHCQAAQNTAGGDLQATSSIIA, (SEQ ID NO: 19)
GDCAGLVSVFGSVHCQSSKNKAGGDLQATSILTTYWPH, (SEQ ID NO: 20)
SDCAKIVSVFGSVHCQSSKNSAGGDLQATSVFTTYWPH, (SEQ ID NO: 21)
SGPSNFVNHAPGEAIVTGLEKGADKVAGTISHTIWEVI, (SEQ ID NO: 22)
QRHSIVQPPAPPPNAFVEIVSSSTGIIIAVGIFAFIFS, (SEQ ID NO: 21)
SGPSNFVNHAPGEAIVTGLEKGADKVAGTISHTIWEVI.
```

Further specific examples of peptides according to the invention include, but are not limited to, peptides that contain 5-all contiguous amino acids from one of the following sequences:

```
RMPPGSCNGATAVFGNVH,                  (SEQ ID NO: 7)

RMPPGSCNGATAIFGNVH,                  (SEQ ID NO: 23)

GDCAGLVSVFGSVHCQSS,                  (SEQ ID NO: 24)

SDCAKIVSVFGSVHCQSS,                  (SEQ ID NO: 25)

QRHSIVQPPAPPPNAFVE,                  (SEQ ID NO: 26)

SGPSNFVNHAPGEAIVTG.                  (SEQ ID NO: 27)
```

These peptides can be linked at either terminus to a polycationic peptide sequence or other nucleic acid binding moiety. The invention also includes variants on these peptides that have at least about 50, 60, 70, 75, 80, 85, 90, 95 or 99% sequence identity to one of the peptides.

These fusogenic peptides can be used directly in this form for preparing the transfection complexes of the present invention. Advantageously, however, the fusogenic peptides are linked to a nucleic acid binding moiety (or other macromolecule binding moiety) to facilitate efficient transfection. The nucleic acid binding moiety can be any of the many known moieties that are used for binding to nucleic acids. Advantageously the binding moiety is cationic or polycationic such that it binds via electrostatic attraction to the polyanionic nucleic acid. Suitable nucleic acid binding moieties include polycationic peptides, such as peptides containing a high percentage of lysine and/or arginine residues, polyamines such as spermine or spermidine or the like, and peptide nucleic acids. Other nucleic acid binding moieties are well known in the art.

The fusogenic peptide is functionally linked to the nucleic acid binding moiety such that when a transfection complex is formed the nucleic acid that is to be transfected is associated with the fusogenic peptide sufficiently that the transfection is enhanced over that observed in the absence of the fusogenic peptide. This is advantageously achieved by covalently linking the fusogenic peptide to the nucleic acid binding domain, although a non-covalent association also can be used. To achieve non-covalent association of the fusogenic peptide and the nucleic acid binding domain, for example, the peptide and the binding domain can respectively be covalently linked to a member of a specific binding pair. For example, the fusogenic peptide can be coupled to biotin and the binding domain could be coupled to streptavidin. Alternatively, the peptide can be linked to a hapten and the binding domain can be coupled to an antibody or antibody fragment, such as an scFv.

Advantageously, however, the fusogenic peptide and the nucleic acid binding domain are covalently linked Suitable linkers for achieving such linkages are well known in the art and are commercially available, for example, from Pierce (Rockford, Ill.). The fusogenic peptide can be derivatized with a bifunctional linker during peptide synthesis and this linker can then be used to form a covalent bond to the nucleic acid binding domain. Alternatively, a nucleophilic amino acid derivative can be introduced into the fusogenic peptide sequence during synthesis, and this derivative can be used to couple the peptide to the nucleic acid binding domain.

Most conveniently, the fusogenic peptide is covalently linked to a polycationic peptide sequence during peptide synthesis. Suitable polycationic peptide sequences contain multiple lysine, ornithine and/or arginine residues, although other basic amino acids also can be used including non-naturally occurring amino acids. Typically, a polycationic peptide will contain 10-30 lysine, ornithine, or arginine residues, and will be 5 to about 50 amino acids long, although the skilled artisan will recognize that any peptide sequence that electrostatically binds to nucleic acids can be used. Advantageously, the polycationic peptide contains 15-20 basic residues and is 15-30 amino acids long.

Specific examples of peptides according to the invention include, but are not limited to, peptides that are 20 to 50 amino acids long and that contain 5-30 contiguous amino acids from one of the following sequences, covalently linked to between 15 and 20 contiguous lysine residues:

```
                                            (SEQ ID NO: 1)
MLRMPPGSCNGATAVFGNVHCQAAQNTAGGDLQATSSIIA, (SEQ ID NO: 2)
MPRMPPGSCNGATAVFGNVHCQAAQNTAGGDLQATSSIIA, (SEQ ID NO: 3)
MSGDCAGLVSVFGSVHCQSSKNKAGGDLQATSILTTYWPH, (SEQ ID NO: 4)
MSSDCAKIVSVFGSVHCQSSKNSAGGDLQATSVFTTYWPH, (SEQ ID NO: 6)
MGSGPSNFVNHAPGEAIVTGLEKGADKVAGTISHTIWEVI, (SEQ ID NO: 5)
MGQRHSIVQPPAPPPNAFVEIVSSSTGIIIAVGIFAFIFS, (SEQ ID NO: 6)
MGSGPSNFVNHAPGEAIVTGLEKGADKVAGTISHTIWEVI.
```

Further specific examples of peptides according to the invention include, but are not limited to, peptides that contain 5-30 contiguous amino acids from one of the following sequences, covalently linked to between 15 and 20 contiguous lysine residues:

```
                                           (SEQ ID NO: 17)
RMPPGSCNGATAVFGNVHCQAAQNTAGGDLQATSSIIA, (SEQ ID NO: 18)
RMPPGSCNGATAIFGNVHCQAAQNTAGGDLQATSSIIA, (SEQ ID NO: 19)
GDCAGLVSVFGSVHCQSSKNKAGGDLQATSILTTYWPH, (SEQ ID NO: 20)
SDCAKIVSVFGSVHCQSSKNSAGGDLQATSVFTTYWPH, (SEQ ID NO: 21)
SGPSNFVNHAPGEAIVTGLEKGADKVAGTISHTIWEVI, (SEQ ID NO: 22)
QRHSIVQPPAPPPNAFVEIVSSSTGIIIAVGIFAFIFS, (SEQ ID NO: 21)
SGPSNFVNHAPGEAIVTGLEKGADKVAGTISHTIWEVI.
```

Further specific examples of peptides according to the invention include, but are not limited to, one of the following sequences:

```
                                           (SEQ ID NO: 28)
RMPPGSCNGATAVFGNVHKKKKKKKKKKKKKKKK (SEQ ID NO: 29)
RMPPGSCNGATAIFGNVHKKKKKKKKKKKKKKKKK
```

-continued

GDCAGLVSVFGSVHCQSSKKKKKKKKKKKKKKKK, (SEQ ID NO: 30)

SDCAKIVSVFGSVHCQSSKKKKKKKKKKKKKKKK, (SEQ ID NO: 31)

QRHSIVQPPAPPPNAFVEKKKKKKKKKKKKKKKK, (SEQ ID NO: 32)

SGPSNFVNHAPGEAIVTGKKKKKKKKKKKKKKKK. (SEQ ID NO: 33)

These peptides contain 16 lysine residues that confer the ability to bind to nucleic acids on the peptide. It will be recognized that the present invention also includes peptides where some or all of these lysine residues are replaced by other positively charged amino acid residues.

Transfection Agents

An additional component of the complexes used in the present invention is a transfection agent. Suitable transfection agents in the context of the present invention include cationic and polycationic polymers, and/or cationic and polycationic lipids. Cationic and polycationic polymers suitable for use in the invention are known in the art and include, for example, dense star dendrimers, PAMAM dendrimers, NH$_3$ core dendrimers, ethylenediamine core dendrimers, dendrimers of generation 5 or higher, dendrimers with substituted groups, dendrimers comprising one or more amino acids, grafted dendrimers and activated dendrimers, polyethyleneimine, polyethyleneimine conjugates, and polyalkylenimine. The skilled artisan will recognize that the present invention is not limited to use of these polycationic polymer transfection agents.

Advantageously, the transfection agent is a lipid, preferably a cationic lipid (or a mixture of a cationic lipid and neutral lipid). This lipid can be used to form a peptide- or protein-nucleic acid-lipid aggregate which facilitates introduction of the anionic nucleic acid through cell membranes, including the nuclear membrane. Transfection compositions of this invention comprising peptide- or protein-nucleic acid complexes and lipid can further include other non-peptide agents that are known to further enhance transfection.

Inclusion of a peptide- or protein-nucleic acid complex or a modified peptide- or protein-nucleic acid complex in a cationic lipid transfection composition can significantly enhance transfection (by 2-fold or more) of the nucleic acid compared to transfection of the nucleic acid mediated by the cationic lipid alone. Enhancement of polycationic polymer transfection by peptides or proteins or modified peptides or modified proteins or fragments thereof of the present invention is pronounced in a wide variety of cell lines, including human primary cell lines and in cell lines that are generally considered by those in the art to be "hard-to-transfect."

Monovalent or polyvalent cationic lipids are employed in cationic lipid transfecting compositions. Illustrative monovalent cationic lipids include DOTMA (N-[1-(2.3-dioleoyloxy)-propyl]-N,N,N-trimethyl ammonium chloride), DOTAP (1,2-bis(oleoyloxy)-3-3-(trimethylammonium)propane), DMRIE (1,2-dimyristyloxypropyl-3-dimethyl-hydroxy ethyl ammonium bromide), DDAB (dimethyl dioctadecyl ammonium bromide), DC-Chol (3-(dimethylaminoethane)-carbamoyl-cholestrerol). Preferred polyvalent cationic lipids are lipospermines, specifically, DOGS (Dioloctadecylaminoglycyl spermine), DOSPA (2,3-dioleyloxy-N-[2(sperminecarboxamido)ethyl]-N,N-dimethyl-1-propanaminium trifluoro-acetate) and DOSPER (1,3-dioleoyloxy-2-(6-carboxy spermyl)-propyl-amid; N-1-dimethyl-N-1-(2,3-dialkyloxypropyl)-2-hydroxypropane-1,3-diamine including but not limited to N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine; N-1-dimethyl-N-1-(2,3-dialkyloxypropyl)-2-(3-amino-2-hydroxypropyloxy)propane-1,3-diamine including but not limited to N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine; and the di- and tetra-alkyl-tetra-methyl spermines, including but not limited to TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldioleyl spermine); and 1,4,-bis[(3-amino-2-hydroxypropyl)-alkylamino]-butane-2,3-diol including but not limited to 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol; and 1,4-bis(3-alkylaminopropyl)piperazine including but not limited to 1,4-bis[(3-oleylamino)propyl]piperazine, 1,4-bis[(3-myristylamino)propyl]piperazine, 1,4-bis[(3-palmitylamino)propyl]piperazine; and a 1,4-bis[(3-(3-aminopropyl)-alkylamino)propyl)piperazine including but not limited to 1,4-bis[(3-(3-aminopropyl)-oleylamino)propyl]piperazine, 1,4-bis[(3-(3-aminopropyl)-myristylamino)propyl]piperazine, 1,4-bis[(3-(3-aminopropyl)-palmitylamino)propyl]piperazine; and 1,4-bis[(3-(3-amino-2-hydroxypropyl)-alkylamino)propyl]piperazine including but not limited to 1,4-bis[(3-(3-amino-2-hydroxypropyl)-oleylamino)propyl]piperazine, 1,4-bis[(3-(3-amino-2-hydroxypropyl)-myristylamino)propyl]piperazine, 1,4-bis[(3-(3-amino-2-hydroxypropyl)-palmitylamino)propyl]piperazine, 1,4-bis[(3-(3-aminopropyl)-alkylamino)-2-hydroxy-propyl]piperazine including but not limited to 1,4-bis[(3-(3-aminopropyl)-oleylamino)-2-hydroxy-propyl]piperazine, 1,4-bis[(3-(3-aminopropyl)-myristylamino)-2-hydroxy-propyl]piperazine, 1,4-bis[(3-(3-aminopropyl)-palmitylamino)-2-hydroxy-propyl]piperazine In certain illustrative examples the cationic lipid is a lipid of Formula (I) such as a 1,4-bis[(3-(3-aminopropyl)-alkylamino)-2-hydroxy-propyl]piperazine, as described in more detail below. Other cationic lipids that may be used include the commercial agents LipofectAmine™ 2000, LipofectAmine™, Lipofectin®, DMRIE-C, CellFectin® (Invitrogen), Oligofectamine® (Invitrogen), LipofectAce® (Invitrogen), Fugene® (Roche, Basel, Switzerland), Fugene® HD (Roche), Transfectam® (Tranfectam, Promega, Madison, Wis.), Tfx-10® (Promega), Tfx-20® (Promega), Tfx-50® (Promega), Transfectin™ (BioRad, Hercules, Calif.), SilentFect™ (Bio-Rad), Effectene® (Qiagen, Valencia, Calif.), DC-chol (Avanti Polar Lipids), GenePorter® (Gene Therapy Systems, San Diego, Calif.), DharmaFect 1® (Dharmacon, Lafayette, Colo.), DharmaFect 2® (Dharmacon), DharmaFect 3® (Dharmacon), DharmaFect 4® (Dharmacon), Escort™ III (Sigma, St. Louis, Mo.) and Escort™ IV (Sigma).

Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. The ratio can vary from 1:1 (molar) to 4:1 (molar) of cationic to neutral lipids. Transfection properties of cationic lipid compositions composed of a 1:1 to 4:1 mixtures of 1,4-bis[(3-(3-aminopropyl)-oleylamino)propyl]piperazine and DOPE and a 1:1 to 4:1 mixtures of 1,4-bis[(3-(3-aminopropyl)-oleylamino)propyl]piperazine and cholesterol as well as a 1:1 to 4:1 mixtures of 1,4-bis[(3-(3-aminopropyl)-palmitylamino)propyl]piperazine and DOPE and a 1:1 to 4:1 mixture of 1,4-bis[(3-(3-aminopropyl)-palmitylamino)propyl]piperazine and cholesterol are significantly enhanced by peptides and proteins of the invention.

Transfection properties of cationic lipid compositions composed of a 1:1 to 4:1 mixtures of 1,4-bis[(3-(3-amino-2-hydroxypropyl)-oleylamino)propyl]piperazine and DOPE and a 1:1 to 4:1 mixtures of 1,4-bis[(3-(3-amino-2-hydroxypropyl)-oleylamino)propyl]piperazine and cholesterol as well as a 1:1 to 4:1 mixtures of 1,4-bis[(3-(3-amino-2-hydroxypropyl)-palmitylamino)propyl]piperazine and DOPE and a 1:1 to 4:1 mixture of 1,4-bis[(3-(3-amino-2-hydroxypropyl)-palmitylamino)propyl]piperazine and cholesterol are significantly enhanced by peptides and proteins of the invention.

A cationic lipid composition composed of a 3:1 (w/w) mixture of DOSPA and DOPE or a 1:1 (w/w) mixture of DOTMA and DOPE is generally useful in transfecting compositions of this invention, although it will be appreciated that many other compositions can be used. Preferred transfection compositions are those which induce substantial transfection of a higher eukaryotic cell line. Inclusion of a peptide- or protein-nucleic acid or modified peptide- or protein-nucleic acid complex in a polycationic polymer transfection composition can significantly enhance transfection (by 2-fold or more) of the nucleic acid compared to transfection of the nucleic acid mediated by the polycationic polymer (e.g. dendrimer) alone or in combination with DEAE-dextran or chloroquine or both. Enhancement of transfection by peptides, proteins, modified peptides or modified proteins is pronounced in a wide variety of cell lines, including human primary cell lines and in cell lines that are generally considered by those in the art to be "hard-to-transfect."

Preparation of the Lipids of Formula (I):

The lipids of Formula I can be synthesized as described generally below and as described in more detail in the examples. Those skilled in the art will recognize that other members of these classes of lipids can be synthesized using variations of these methods or other methods that are well known in the art.

An amine-containing cyclic moiety such as 1,4-bis(3-amino-2-hydroxypropyl)piperazine may be prepared, for example, by alkylation of piperazine with N-(2,3-epoxypropyl)phthalimide, followed by removal of the phthalamide group using hydrazine hydrate. The resulting 1,4-bis(-3-amino-2-hydroxypropyl)piperazine may be acylated with an activated carboxyl compound, for example and alkyl acid chloride or alkenyl acid chloride such as oleoyl chloride. The resulting amide may be reduced, for example with lithium aluminum hydride, and the resulting secondary amine alkylated using a haloalkylphthalimide, such as 3-bromopropylpthalimide. The phthalimide moiety may be removed using, for example, hydrazine hydrate and the resulting amine may be protonated with an acid such as HCl or trifluoroacetic acid to obtain the desired cationic lipids. The skilled artisan will recognize that this general reaction scheme can be used to prepare a wide variety of cationic lipids of the present invention. For example, 1,4-bis[(3-(3-aminopropyl)-oleylamino)-2-hydroxypropyl]piperazine or 1,4-bis[(3-(3-aminopropyl)-alkylamino)-2-hydroxypropyl]piperazine, where alkyl can constitute a $C_{10}$-$C_{30}$ alkyl chain, can be synthesized.

Substituted heterocyclic rings can be prepared using methods that are well known in the art. For example, disubstituted piperazine moieties may be prepared from diketopiperazine compounds by reduction of the lactam groups with a suitable reducing agent, as described, for example, in *J. Med. Chem.* 39:1345 (1996).

Transfection Enhancing Agents

The complexes formed between the fusogenic peptide, the optional nucleic acid binding domain, the nucleic acid and the transfection agent may be further enhanced by inclusion of moieties such as proteins or peptides that function for nuclear or other sub-cellular localization, function for transport or trafficking, are receptor ligands, comprise cell-adhesive signals, cell-targeting signals, cell-internalization signals or endocytosis signals as well as peptides or functional portions thereof of viral fusogenic proteins of enveloped viruses, of viral nuclear localization signals, of receptor-ligands, of cell adhesion signals, of cell-targeting signals or of internalization- or endocytosis-triggering signals.

Examples of transfection enhancing agents include, but are not limited to, insulin, a transferrin, epidermal growth factor, fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, a arginine rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, and fragments thereof.

Any proteins or peptides (or fragments or portions thereof) of the invention may be used in accordance with this invention, either singly or in combination with other proteins or peptides. In a preferred aspect, two or more, three or more, four or more, five or more, six or more, etc. proteins and/or peptides are used in the invention. Additionally, such single or multiple proteins and/or peptides may be used in combination with one or more, two or more, three or more, four or more, five or more, six or more, etc. transfection agents. In another preferred aspect, at least two peptides and/or proteins are used in combination with a transfection agent, preferably at least two transfection agents such as lipids, and/or polycations such as dendrimers or PEI.

Preparation and Use of Complexes Containing Fusogenic Peptides

The methods of the present invention involve contacting any cell, preferably a eukaryotic cell, with a transfection complex comprising at least a fusogenic peptide, a transfection agent and a nucleic acid as described above. The complex optionally may also contain one or more additional peptides or proteins, such as a fusogenic, membrane-permeabilizing, transport or trafficking sub-cellular-localization, or receptor-ligand peptide or protein. These additional peptides or proteins optionally may be conjugated to a nucleic acid-binding group, or optionally conjugated to the transfection agent (lipid or polycationic polymer) where the peptide or protein or modified peptide or protein is non-covalently associated with the nucleic acid. Without being bound by any theory, applicants believe that the complexes of the present invention are lipid aggregates that typically contain liposomal structures, although the precise nature of these structures is not presently known. Accordingly, in certain illustrative examples, complexes of the present invention are liposomal complexes. The entire complex, or a portion of the complex, such as a lipid portion, for example a lipid of Formula I, can be formulated into liposomes, for example using the method of reverse evaporation, which is well known in the art. Alternatively the lipid portion of the complex or the entire complex, can be formulated by other well known methods for liposome formation such as sonication or microfluidization. These liposome formulations are effective for transfecting DNA into cultured cells.

In one embodiment, a complex containing the fusogenic peptide- or protein of the invention and the nucleic acid (where the fusogenic peptide or protein can be conjugated to a nucleic-acid binding group) is first formed and then combined with a cationic lipid, such as a lipid of Formula I, for transfection. In a related embodiment, a peptide- or protein-lipid conjugate is combined optionally with other lipids, including any appropriate cationic lipid, and then combined with nucleic acid for transfection. In another related embodiment, a nucleic acid-lipid complex is formed and then combined with a fusogenic peptide or protein for transfection. As discussed above, the lipid-containing complexes of any of these embodiments can be liposomal or non-liposomal formulations. Furthermore, any of the complexes formed in these embodiments can be stored, for example, for 5 minutes to 1 year, or for 15 minutes to 6 months, or for 1 hour to 3 months, before transfecting cells. In the case of a peptide or protein-lipid conjugate, such a conjugate can be stored for example, for 5 minutes to 1 year, or for 15 minutes to 6 months, or for 1 hour to 3 months, before combining with nucleic acid.

In another embodiment, a complex containing the fusogenic peptide or protein and the nucleic acid (where the fusogenic peptide or protein can be conjugated to a nucleic-acid binding group) is formed and then combined with a polycationic polymer for transfection. In a related embodiment, a peptide-polycationic polymer conjugate is combined optionally with another polycationic polymer and then combined with nucleic acid for transfection. In another related embodiment, a nucleic acid-polycationic polymer complex is formed and then combined with a peptide or protein for transfection. A polycationic polymer and/or peptide-conjugated polycationic polymer can be combined with cationic lipids and cationic lipid composition to obtain improved nucleic acid transfection compositions. In accordance with the invention, multiple peptides and/or proteins may be added to accomplish transfection.

Transfection compositions of this invention comprising peptide- or protein-lipid conjugates and nucleic acids can further include other non-peptide or non-protein agents that are known to further enhance transfection.

Transfection compositions of this invention comprising peptide- or protein-polycationic polymer conjugates and nucleic acid can further include other non-peptide agents that are known to further enhance polycationic polymer transfection, for example polycationic polymer transfection can be enhanced by addition of DEAE-dextran and/or chloroquine.

In one specific embodiment, the fusogenic peptide or protein, advantageously containing a polycationic sequence of amino acids, is first bound to a nucleic acid to be introduced into a cell. The peptide- or protein-nucleic acid complexes are then admixed with a transfection agent (or mixture of agents) and the resulting mixture is employed to transfect cells. Preferred transfection agents are cationic lipid compositions, such as those containing a lipid of Formula (I), particularly monovalent and polyvalent cationic lipid compositions, more particularly cationic lipid compositions composed of a 1:1 to 4:1 mixtures of 1,4-bis[(3-(3-aminopropyl)-oleylamino)propyl]piperazine and DOPE and a 1:1 to 4:1 mixtures of 1,4-bis[(3-(3-aminopropyl)-oleylamino)propyl]piperazine and cholesterol as well as a 1:1 to 4:1 mixtures of 1,4-bis[(3-(3-aminopropyl)-palmitylamino)propyl]piperazine and DOPE and a 1:1 to 4:1 mixture of 1,4-bis[(3-(3-aminopropyl)-palmitylamino)propyl]piperazine and cholesterol; cationic lipid compositions composed of a 1:1 to 4:1 mixtures of 1,4-bis[(3-(3-amino-2-hydroxypropyl)-oleylamino)propyl]piperazine and DOPE and a 1:1 to 4:1 mixtures of 1,4-bis[(3-(3-amino-2-hydroxypropyl)-oleylamino)propyl]piperazine and cholesterol as well as a 1:1 to 4:1 mixtures of 1,4-bis[(3-(3-amino-2-hydroxypropyl)-palmitylamino)propyl]piperazine and DOPE and a 1:1 to 4:1 mixture of 1,4-bis[(3-(3-amino-2-hydroxypropyl)-palmitylamino)propyl]piperazine and cholesterol; cationic lipid compositions composed of a 1:1 to 4:1 mixtures of 1,4-bis[(3-(3-aminopropyl)-oleylamino)-2-hydroxy-propyl]piperazine and DOPE and a 1:1 to 4:1 mixtures of 1,4-bis[(3-(3-aminopropyl)-oleylamino)-2-hydroxy-propyl]piperazine and cholesterol as well as a 1:1 to 4:1 mixtures of 1,4-bis[(3-(3-aminopropyl)-palmitylamino)-2-hydroxy-propyl]piperazine and DOPE and a 1:1 to 4:1 mixture of 1,4-bis[(3-(3-aminopropyl)-palmitylamino)-2-hydroxy-propyl]piperazine and cholesterol.

In a second specific transfection method, a transfection-enhancing peptide or protein is conjugated to a nucleic acid-binding group, for example a polyamine and more particularly a spermine, to produce a modified peptide or protein which is then bound to the nucleic acid to be introduced into the cell. The modified peptide-nucleic acid complex is then admixed with a transfection agent (or mixture thereof) and the resulting mixture is employed to transfect cells. In particular, the peptide or protein is covalently conjugated to a spermine, the spermine-modified peptide or protein is complexed with nucleic acid and admixed with a cationic lipid. Preferred transfection agents are cationic lipid compositions, particularly monovalent and polyvalent cationic lipid compositions, more particularly cationic lipid compositions composed of a 1:1 to 4:1 mixtures of 1,4-bis[(3-(3-aminopropyl)-oleylamino)propyl]piperazine and DOPE and a 1:1 to 4:1 mixtures of 1,4-bis[(3-(3-aminopropyl)-oleylamino)propyl]piperazine and cholesterol as well as a 1:1 to 4:1 mixtures of 1,4-bis[(3-(3-aminopropyl)-palmitylamino)propyl]piperazine and DOPE and a 1:1 to 4:1 mixture of 1,4-bis[(3-(3-aminopropyl)-palmitylamino)propyl]piperazine and cholesterol; cationic lipid compositions composed of a 1:1 to 4:1 mixtures of 1,4-bis[(3-(3-amino-2-hydroxypropyl)-oleylamino)propyl]piperazine and DOPE and a 1:1 to 4:1 mixtures of 1,4-bis[(3-(3-amino-2-hydroxypropyl)-oleylamino)propyl]piperazine and cholesterol as well as a 1:1 to 4:1 mixtures of 1,4-bis[(3-(3-amino-2-hydroxypropyl)-palmitylamino)propyl]piperazine and DOPE and a 1:1 to 4:1 mixture of 1,4-bis[(3-(3-amino-2-hydroxypropyl)-palmitylamino)propyl]piperazine and cholesterol; cationic lipid compositions composed of a 1:1 to 4:1 mixtures of 1,4-bis[(3-(3-aminopropyl)-oleylamino)-2-hydroxy-propyl]piperazine and DOPE and a 1:1 to 4:1 mixtures of 1,4-bis[(3-(3-aminopropyl)-oleylamino)2-hydroxy-propyl]piperazine and cholesterol as well as a 1:1 to 4:1 mixtures of 1,4-bis[(3-(3-aminopropyl)-palmitylamino)-2-hydroxy-propyl]piperazine and DOPE and a 1:1 to 4:1 mixture of 1,4-bis[(3-(3-aminopropyl)-palmitylamino)-2-hydroxy-propyl]piperazine and cholesterol.

In a third specific embodiment, a mixture of one or more transfection-enhancing peptides, proteins, or protein fragments, including fusogenic peptides or proteins, transport or trafficking peptides or proteins, receptor-ligand peptides or proteins, or nuclear localization peptides or proteins and/or their modified analogs (e.g., spermine modified peptides or proteins) or combinations thereof are mixed with amino acid sequences from fusogenic proteins of non enveloped and complexed with nucleic acid to be introduced into a cell. The peptide-nucleic acid complexes are then admixed with transfection agent and the resulting mixture is employed to transfect cells. In certain embodiments, the mixture of the transfection enhancing peptide, protein, or protein fragment is stored before it is complexed with nucleic acid.

In another specific embodiment, a component of a transfection agent (lipids, cationic lipids, dendrimers, or PEI) is covalently conjugated to selected peptides, proteins, or protein fragments directly or via a linking or spacer group. Of particular interest in this embodiment are peptides or proteins that are fusogenic proteins from non-enveloped viruses.

Exemplary Uses of the Complexes Containing Fusogenic Peptides of Non-Enveloped Viruses The complexes and methods of the present invention, especially those involving transfection compositions that include complexes provided herein, can be used for in vitro and in vivo transfection of cells, particularly of eukaryotic cells, and more particularly to transfection of higher eukaryotic cells, including animal cells. The methods of this invention can be used to generate transfected cells which express useful gene products. The methods of this invention can also be employed as a step in the production of transgenic animals. The methods of this invention are useful as a step in any therapeutic method requiring introduction of nucleic acids into cells including methods of gene therapy and viral inhibition and for introduction of antisense or antigene nucleic acids, ribozymes, RNA regulatory sequences, siRNA, RNAi, Stealth™ RNAi (Invitrogen Corporation, Carlsbad Calif.) or related inhibitory or regulatory nucleic acids into cells. In particular, these methods are useful in cancer treatment, in in vivo and ex vivo gene therapy, and in diagnostic methods.

The transfection compositions and methods of this invention comprising peptides, proteins, peptide or protein fragments or modified peptides or modified proteins, can also be employed as research agents in any transfection of eukaryotic cells done for research purposes.

Accordingly, provided herein is a method of introducing a macromolecule into a cell, that includes forming a transfection composition that includes a nucleic acid and a complex comprising a transfection agent and a fusion agent, wherein the fusion agent includes a fusion promoting amino acid sequence derived from a fusion protein of a non-enveloped virus; and contacting a eukaryotic cell with the transfection composition. Provided in the Examples section herein are illustrative protocols for using compositions of the present invention to transfect eukaryotic cells. As disclosed herein, the fusion agent in illustrative examples is a fusion peptide derived from a FAST protein of a Reovirus, advantageously a fusion peptide that is between 5 and 50 amino acids in length where at least 10 contiguous amino acids of the fusion peptide are at least 75, 80, 85, 90, 95 or 100% identical to a hydrophobic region of a Reovirus FAST protein, and a polycationic peptide sequence.

As illustrated in the Examples section below, volumes and concentrations of nucleic acid or other macromolecule, volume and concentration of the transfection complexes provided herein, volumes and compositions of diluents, and volume and concentration of cells, can be determined using standard experimental approaches for such optimization and titration, including, for example, methods that utilize cytotoxicity assays and/or methods that employ transfection using nucleic acid expression vectors that express reporter genes, such as beta galactosidase, luciferase, and/or fluorescent proteins. Furthermore, cell densities can be optimized using standard methods, and cell densities for transfections using the transfection complexes provided herein can range, for example, from high density >75% to low density <50%

Exemplary diluents for complex formation, for example, include reduced-serum, or serum-free media, such as D-MEM and RPMI 1640 and OptiPro™, Opti-MEM® (Invitrogen Corporation). Incubation times for forming complexes can be determined using routine methods, although typical incubation times are between 5 and 240 minutes. In addition, it will be understood that media for culturing of cells before and after transfection can be chosen based on the cell line to be transfected and based on the particular application of the method. For example, for the production of proteins in suspension cells, in illustrative embodiments, reduced serum, or advantageously serum-free, medium can be used. In certain illustrative embodiments, animal origin-free medium is employed, such as, but not limited to, 293 Expression Medium (Invitrogen Corporation) and CD-CHO Medium (Invitrogen Corporation). In certain aspects depending on the cell type to be transfected, antibiotics can be excluded from post-transfection media. Incubation times for post-transfection culturing of cells varies depending on the cell type and the desired outcome of the transfection, but typically ranges from 2 hours to 7 days. For large-scale protein production, cells can be incubated, as a non-limiting example, for between 1 day and 7 days.

It will be understood that a wide range of concentrations of transfection agent and a fusion agent can be used in the complexes, compositions and methods provided herein. For example, in an illustrative non-limiting example of a composition that includes a complex of a cationic lipid and a fusogenic peptide, the total exemplary, non-limiting combined concentration of cationic lipid and fusogenic peptide in the composition can be between 1 mg/ml and 4 mg/ml. The range of peptide added to the lipid at 1 mg/ml can between 100 µgml and 3 mg/ml. the ratio of the cationic lipid to helper lipid can between 0.5/1.0 (molar) and pure compound.

Cells that can be transfected according to the present invention include, for example, virtually any eukaryotic cell including primary cells, cells in culture, and cells in cultured tissue. The cells can be attached cells or cells in suspensions. In certain illustrative aspects, the cells are suspension CHO-S cells and suspension 293-F cells. Suspension cell cultures are particularly well-suited for protein production methods provided herein. Other cells that can be transfected using the agents and methods of the invention include, but are not limited to, 293, such as GripTite 293 MSR (Invitrogen Corporation), CHO, Cos7, NIH3T3, Hela, primary fibroblast, A549, Be2C, SW480, Caco2, primary neurons. Jurkat, C6, THP1, IMR90, HeLa, ChoK1, GT293, MCF7, HT1080, LnCap, HepG2, PC12, SKBR3, and K562 cells.

In certain embodiments provided herein, a transfection enhancing agent is included in the complex that is used to transfect cells. For example the transfection enhancing agent can be a nuclear localization peptide. In one example, the transfection enhancing agent is the PLUS™ Reagent (Invitrogen Corporation). It has been shown that the addition of PLUS™ reagent enhances protein expression when used together with transfection compositions as provided herein. Expression was enhanced in NIH3T3, Jurkat, C6, Cos7 THP1, IMR90, LnCap, HepG2, PC12 and K562 cells. Cytotoxicity was not affected by the use of the PLUS™ Reagent.

In another embodiment, provided herein is a method for producing a protein comprising, transfecting a cell with a nucleic acid molecule encoding the protein, incubating the cell to produce the protein, and collecting the protein, wherein the transfecting is performed by contacting the cell with a transfection composition of the present invention. The composition for transfecting the cell can be any compositions as provided herein. Exemplary compositions include the nucleic acid molecule encoding the protein of interest, a fusion agent, and typically a transfection agent, where the fusion agent includes a fusion-promoting amino acid sequence derived from a fusion protein of a non-enveloped virus, such as a reovirus protein.

In illustrative embodiments the encoded protein is an antibody molecule, or an antigen binding fragment or derivative portion thereof, for example a single chain Fv fragment. In these embodiments, the method can further include isolating the protein, for example, by using affinity purification on an antibody-binding column. In certain examples, nucleic acids encoding both chains of an antibody are transfected into cells using a transfection composition provided herein.

It will be understood that the nucleic acid encoding the protein can be an expression vector. The expression vector typically has a promoter operatively linked to one or more nucleic acid sequences encoding one or more protein chains. Where the protein produced is a pharmaceutical product, the protein can be formulated accordingly, for example in an appropriate choice of physiologic medium.

The transfection composition provided herein can also be used to introduce peptides and proteins and the like into cells using methods that are known in the art. Methods of using cationic lipids for peptide and protein delivery previously have been described. In addition, the transfection compositions can be used to deliver nucleic acids, peptides and proteins and the like into tissues in vivo. Methods of using lipids for delivering compounds to tissue in vivo previously have been described. The transfection compositions can, with appropriate choice of physiologic medium, be employed in therapeutic and diagnostic applications.

Cell Transfections Using Lipids of Formula (I)

Figure 6:
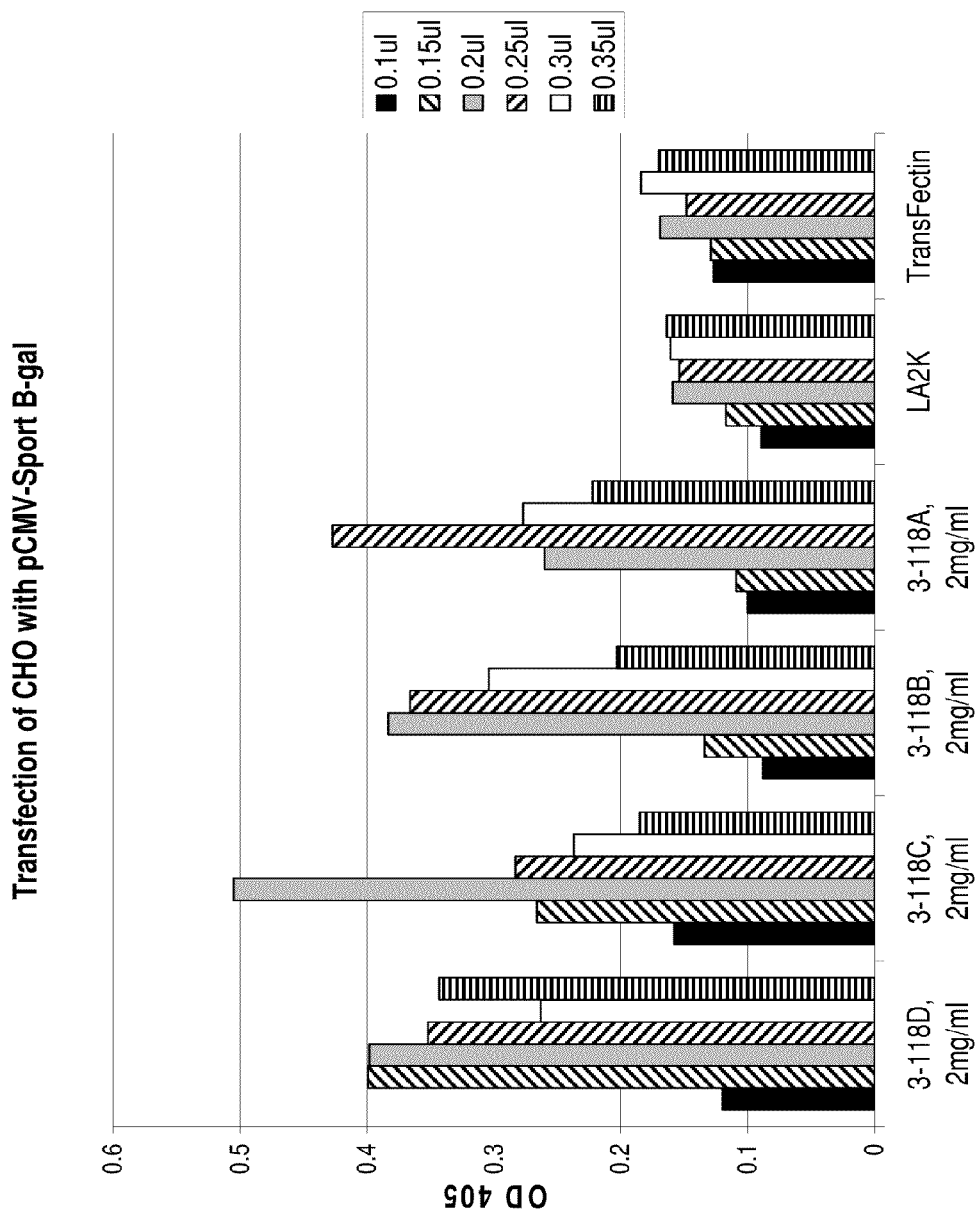
FIG. 6 compares the results obtained from transfection of CHO cells with the plasmid pCMV-Sport β-gal using LipofectAmine2000™, Transfectin™, and various formulations of a compound of the invention. Transfection was carried out using a compound of Formula (I) formulated without a co-lipid (3-118-D) and with cholesterol in a molar ratio of 1:1 (3-118-A), 2:1 (3-118-B) and 4:1 (3-118-C). Transfection with LipofectAmine™ 2000 (LA2K, Invitrogen Corp., Carlsbad, Calif.) and Transfectin™ (BioRad, Hercules, Calif.) also is shown for comparison.
Figure 7:
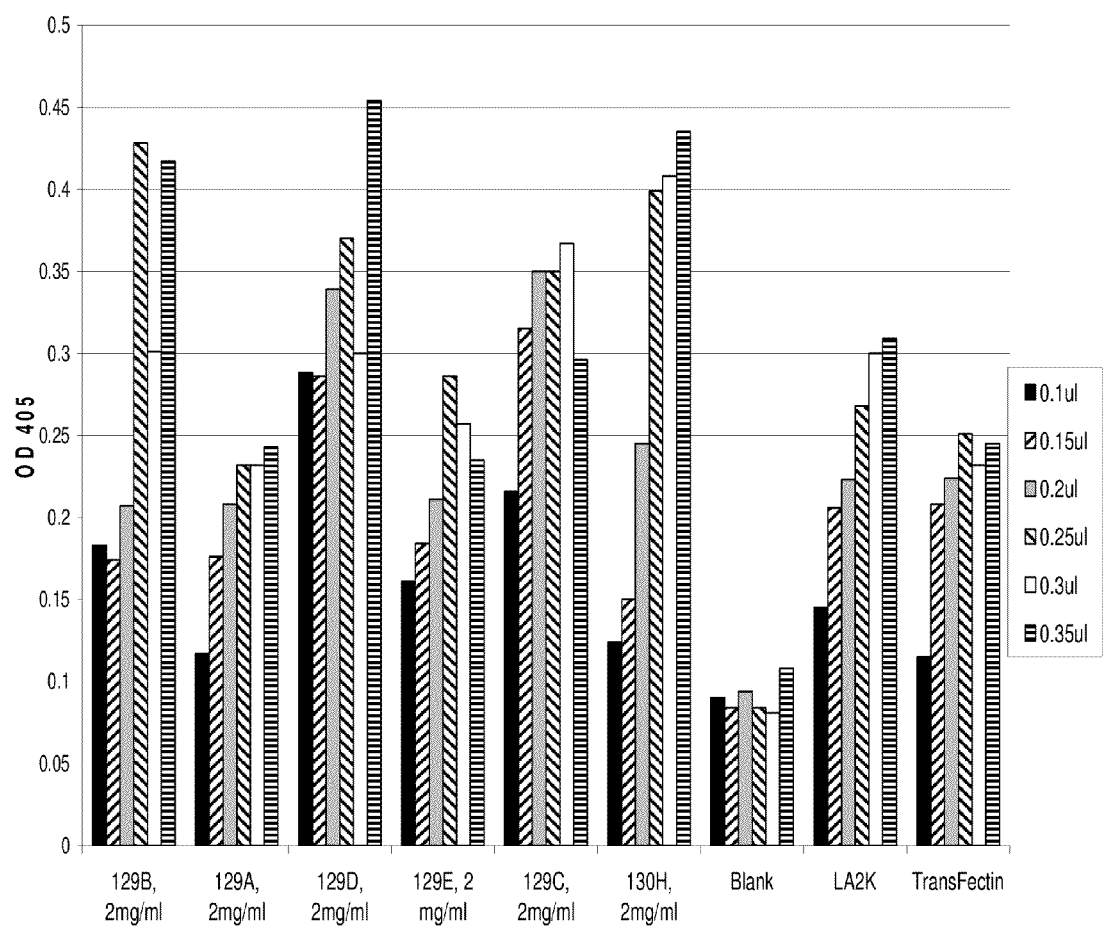
FIG. 7 shows the results obtained from transfection of HEK 293 cells with the plasmid pCMV-Sport β-gal using LipofectAmine™ 2000, Transfectin, and various formulations of a second compound of Formula (I). Transfection was carried out using a compound of the invention formulated without a co-lipid (129E) and with cholesterol in M/M ratio of 1:1 (129H), 2:1 (129C) and 4:1 (129D); and a compound of this invention formulated with DOPE in M/M 2:1 (129A) and 4:1 (129B). Transfection with LipofectAmine™ 2000 (LA2K) and Transfectin™ is shown for comparison
Figure 8:
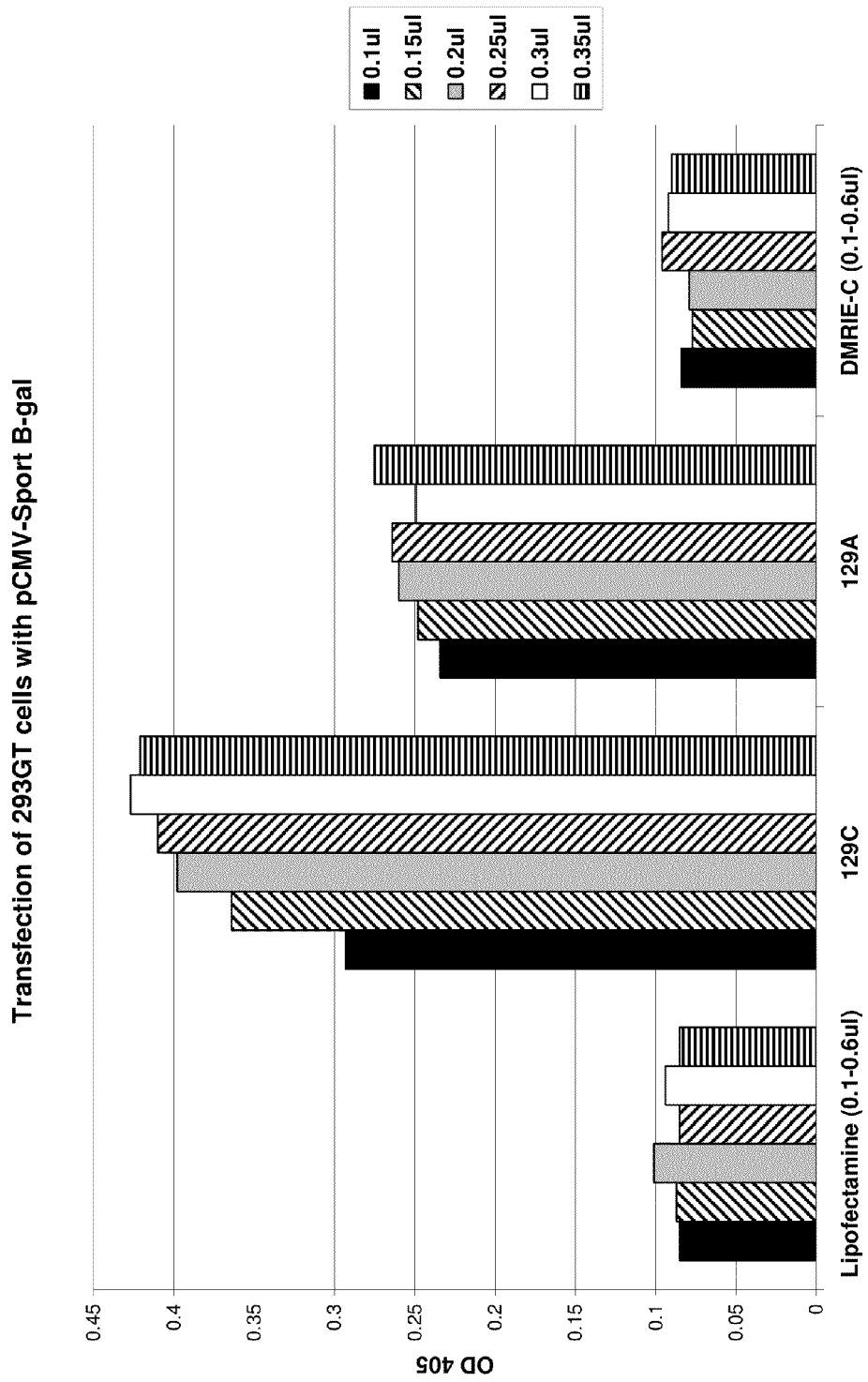
FIG. 8 shows the results obtained from transfection of NIH 3T3 cells with the plasmid pCMV-Sport β-gal using LipofectAmine™ and DMRIE-C (Invitrogen Corp., Carlsbad, Calif.) and various formulations of a second compound of Formula (I). Transfection was carried out using a compound of the invention formulated with cholesterol in M/M ratio of 2:1 (129C); and compound of this invention formulated with DOPE in M/M 2:1 (129A). Transfection with LipofectAmine™ and DMRIE-C is shown for comparison.
Figure 9:
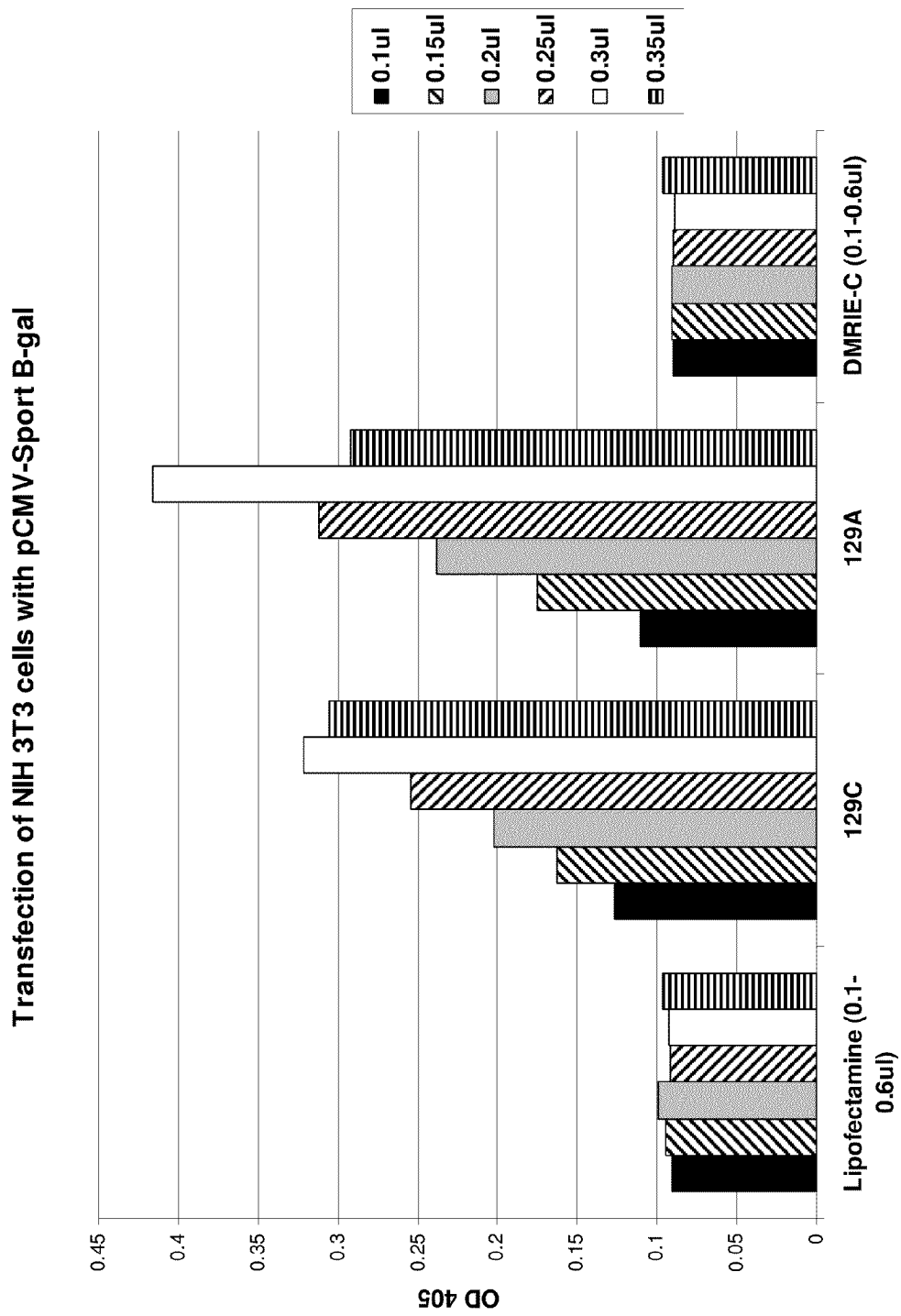
FIG. 9 shows the results obtained from transfection of 293GT cells with the plasmid pCMV-Sport β-gal using LipofectAmine™ and DMRIE-C (Invitrogen Corp., Carlsbad, Calif.) and various formulations of a second compound of Formula (I) Transfection was carried out using a compound of the invention formulated with cholesterol in M/M ratio of 2:1 (129C); and compound of this invention formulated with DOPE in M/M 2:1 (129A). Transfection with LipofectAmine™ and DMRIE-C is shown for comparison.

The lipids of Formula (I) can be used alone for delivery of macromolecules into cells in vitro or in vivo. These lipids are at least as active, and in most cases more active, than cationic lipids that currently are commercially available for delivery of macromolecules into cells. Lipids of the present invention, for example the HCL salt of 1,4-Bis[(3-(3-aminopropyl)-oleoylamino)-2-hydroxypropyl]piperazine, were formulated without co-lipid or with the neutral lipids DOPE or cholesterol (129A-E and 129H in Example 11). As shown in FIGS. 6-9, the lipids of the invention have been used to transfect CHO, NIH3T3, HEK293 and 293GT cells, and were shown to afford transfection efficiencies that were 2-4-fold better than the comparison lipids.

The macromolecules which can be delivered into cells include, but are not limited to, nucleic acids. The nucleic acid can be any type of nucleic acid that presently is known or that may be prepared or identified in the future, provided that the nucleic acid is sufficiently negatively charged to form a lipid aggregate, liposome, or liposome-like complex when admixed with any lipid of Formula (I). Nucleic acid, as used herein, refers to deoxyribonucleotides or ribonucleotides and mixtures and polymers thereof in single- or double-stranded form. The term encompasses nucleic acids containing known nucleotide analogs or modified backbone residues or linkages, which are synthetic, naturally occurring, and non-naturally occurring, which have similar binding properties as a reference nucleic acid, and which are metabolized in a manner similar to a reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The nucleic acid may be in the form of an antisense molecule, for example a "gap-mer" containing an RNA-DNA-RNA structure that activates RNAseH. The nucleic acid can be, for example, DNA or RNA, or RNA-DNA hybrid, and can be an oligonucleotide, plasmid, parts of a plasmid DNA, pre-condensed DNA, product of a polymerase chain reaction (PCR), vectors, expression cassettes, chimeric sequences, chromosomal DNA, or derivatives of these groups or other form of nucleic acid molecule. The nucleic acid may be a double-stranded RNA molecule of the type used for inhibiting gene expression by RNA interference. The nucleic acid may be a short interfering double stranded RNA molecule (siRNA). The nucleic acid molecule can also be a Stealth™ RNAi molecule (Invitrogen Corporation, Carlsbad, Calif.).

Accordingly, provided herein is a method of introducing macromolecules into cells. An exemplary method includes forming a lipid-nucleic acid complex using a lipid of Formula (I) and a nucleic acid, as described herein, and contacting cells, such as, by way of example only, eukaryotic cells, with such a complex. The lipid may be in the form of a lipid-aggregates, including, but not limited to, liposomes. The lipid of Formula (I) may be used with a fusogenic peptide from a non-enveloped virus according to the present invention, to transfect cells. It will be understood that incubation times, mixing protocols, and other specific aspects of the methods of the invention can be optimized using methods known in the art.

Cells which can be transfected according to the such methods include, but are not limited to, virtually any eukaryotic cell including primary cells, cells in culture, a passaged cell culture or a cell line, and cells in cultured tissue. Suitable cells include human cell lines and animal cell lines. The cell may be a fibroblast. The cells can be attached cells or cells in suspensions. In certain illustrative aspects, the cells are suspension CHO-S cells and suspension 293-F cells. Other cells that may be used include, without limitation, 293, 293-S, CHO, Cos, 3T3, Hela, primary fibroblasts, A549, Be2C, SW480, CHOK1, Griptite 293, HepG2, Jurkat, LNCap, MCF-7, NIH-3T3, PC12, C6, Caco-2, COS-7, HL60, HT-1080, IMR-90, K-562, SK-BR3, PHP1, HUVEC, MJ90, NHFF, NDFF and primary neurons.

In another embodiment is a method for producing a protein which includes contacting a cell with a lipid-nucleic acid complex as described above, wherein the nucleic acid encodes the protein. The cells are incubated to produce the protein and the protein is collected. Cells which can be used for protein production are described above. In addition, any composition which includes a lipid of Formula (I) can be used for transfection of cells. Such compositions are further discussed herein, and include, but are not limited to compositions comprising lipids of Formula (I), a co-lipid and an optional transfection enhancing agent such as a fusogenic peptide or protein.

The lipid aggregates of the present invention form a complex when they come in contact with macromolecules such as nucleic acids. The lipids optionally may be used in slight excess and, in such as case, may form a cationic complex. Without being bound by any theory, it is thought that cationic complexes are attracted to the cell membrane thereby facilitating uptake by the cell. Such lipid aggregates include liposomes, unilamellar vesicles, multilamellar vesicles, micelles and the like, which can have particle sizes in the nanometer to micrometer range. The structure of various types of lipid aggregates varies, depending on composition and method of forming the aggregate. Methods of making lipid aggregates are known in the art, and include, but are not limited to, reverse evaporation, sonication and microfluidization.

In another embodiment, provided herein is a method for producing a protein comprising, transfecting a cell with a nucleic acid encoding the protein, incubating the cell to produce the protein, and collecting the protein, wherein the transfecting is performed by contacting the cell with a composition comprising a lipid of formula I, optionally with a fusogenic peptide of a non-enveloped virus. The composition for transfecting the cell can be any of the compositions provided herein, including those that include other lipids and/or additional peptides and proteins.

The lipids of Formula (I) may also be used to introduce peptides and proteins and the like into cells using methods that are known in the art. Methods of using cationic lipids for peptide and protein delivery previously have been described.

In addition, the lipids may be used to deliver nucleic acids, peptides and proteins and the like into tissues in vivo. Methods of using lipids for delivering compounds to tissue in vivo previously have been described.

Cationic lipid compositions composed of 1,4-bis[(3-(3-aminopropyl)-alkylamino)propyl]piperazine lipids and neutral lipids, including 1:1 to 4:1 mixtures of 1,4-bis[(3-(3-aminopropyl)-oleylamino)propyl]piperazine and DOPE and a 1:1 to 4:1 mixtures of 1,4-bis[(3-(3-aminopropyl)-oleylamino)propyl]piperazine and cholesterol as well as a 1:1 to 4:1 mixtures of 1,4-bis[(3-(3-aminopropyl)-palmitylamino)propyl]piperazine and DOPE and a 1:1 to 4:1 mixture of 1,4-bis[(3-(3-aminopropyl)-palmitylamino)propyl]piperazine and cholesterol were effective at transfecting various cell types with nucleic acids.

Compositions and/or Methods that Use Other Lipids and/or Peptides

In certain illustrative examples, the lipids of Formula (I) also can be used in compositions with other lipids and/or with additional transfection-enhancing agents to deliver macromolecules. Such compositions may contain a lipid of Formula (I) and a co-lipid which is neutral, positively charged (such as a cationic lipid) or negatively charged. Such neutral lipids include, but are not limited to, diacylphosphatidylcholine, diacylphosphatidylethanolamine (DOPE), ceramide, sphingomyelin, cephalin, cholesterol, cerebrosides and diacylglycerols. for example. The cationic lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N', N'-dimethylaminoethane)-carbamoyl)cholesterol (DC-Chol); N-(1,2-dimyristyloxyprop-3-yl)-N,N-dimethyl-N-hydroxyethyl ammonium bromide (DMRIE); 1,2-Dilinoleyloxy-N,N-dimethylaminopropane (DLinDMA); 1,2-Dilinolenyloxy-N,N-dimethylaminopropane (DLenDMA), DODAP, DODMA, and DMDMA. The cationic lipids may also include, but are not limited to, LipofectAmine™ 2000, LipofectAmine™, Lipofectin®, DMRIE-C, Fugene®, Fugene® HD, Transfectam®, Transfectin™, SilentFect™, and Effectene®. The anionic lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Transfection enhancing agents which may be included in the compositions described above include, but are not limited to, transfection-enhancing peptides or proteins that function to deliver the macromolecule to specific sub-cellular locations such as the nucleus or other organelles, that function for cellular transport or trafficking, that are receptor ligands, that comprise cell-adhesion signals, cell-targeting signals, cell-internalization signals or endocytosis signals. Other examples include peptides or functional portions thereof that are enveloped or non-enveloped viral proteins or derived from enveloped or non-enveloped viral proteins, that are enveloped or non-enveloped viral fusogenic proteins or derived from enveloped or non-enveloped viral fusogenic proteins, that contain viral nuclear localization signals, that are receptor-ligands, that contain cell adhesion signals, cell-targeting signals, and/or internalization- or endocytosis-triggering signals. Exemplary fusogenic peptides are the reovirus-derived peptides described herein.

In certain embodiments provided herein, transfection enhancing agent can be a nuclear localization peptide. In one example, the transfection enhancing agent is the PLUS™ Reagent (Invitrogen Corporation). It has been determined in initial experiments that the addition of PLUS™ reagent enhances protein expression when used along with transfection compositions provided herein. In fact, expression was enhanced in NIH3T3, Jurkat, C6, Cos7 THP1, IMR90, LnCap, HepG2, PC12 and K562 cells. Cytotoxicity was not affected by the use of the PLUS™ Reagent.

In an illustrative example, the lipids of the present invention are used in conjunction with Plus Reagent™ (available from Invitrogen Corporation, Carlsbad, Calif.), as provided in exemplary transfection protocols provided herein. Furthermore, the lipids can be formulated in liposomal or non-liposomal formulations, that can include a helper lipid, such as DOPE, along with a Prototypical Avian reovirus fusogenic peptide, as described above, and used in conjunction with Plus Reagent™ to deliver nucleic acids to cells.

Exemplary peptides or proteins that may be used in combination with the lipids of formula I include those derived from enveloped and non enveloped viruses, bacteria, insulin, a transferrin, a epidermal growth factor, a fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a reo virus fusion protein or peptide, a histone protein, an arginine rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a adapatin protein, a bacteriacidal-permability-increasing protein, a nisin, a buforin, and fragments thereof.

The novel lipids of Formula (I) may be formulated with one or more nucleic acids into liposomes or liposome-like vehicles in the presence or absence of co-lipid such as, by way of example only, dioleylphosphatidyl ethanolamine (DOPE) or cholesterol. The lipids may be formulated into liposomes, for example using the method of reverse evaporation, which is well known in the art. Alternatively the lipids may be formulated by other well known methods for liposome formation such as sonication, microfluidization etc. These liposome formulations are effective for transfecting DNA into cultured cells.

In one method, a nucleic acid is contacted with a fusion agent and the resulting mixture is added to a mixture of a lipid of Formula (I) and a neutral lipid, where the fusion agent contains a fusion-promoting amino acid sequence derived from a fusion protein of a non-enveloped virus, as described in more detail above and in the Examples below.

In another method, a fusion agent is contacted with a lipid of Formula (I) followed by addition of a nucleic acid or protein capable of aggregating the peptide- or protein-nucleic acid complex, where the fusion agent contains a fusion-promoting amino acid sequence derived from a fusion protein of a non-enveloped virus, as described in more detail above and in the Examples below.

In certain embodiments of the present invention methods involve contacting any cell, preferably a eukaryotic cell, with a transfection complex comprising at least a fusogenic peptide, a lipid of Formula (I) and a nucleic acid as described above. The complex optionally may also contain one or more additional peptides or proteins, such as a fusogenic, membrane-permeabilizing, transport or trafficking sub-cellular-localization, or receptor-ligand peptide or protein. These additional peptides or proteins optionally may be conjugated to a nucleic acid-binding group, or optionally conjugated to a lipid of Formula (I) where the peptide or protein or modified peptide or protein is non-covalently associated with the nucleic acid. Without being bound by any theory, applicants believe that the complexes of the present invention are lipid aggregates that typically contain liposomal structures, although the precise nature of these structures is not presently known. Accordingly, in certain illustrative examples, complexes of the present invention are liposomal complexes. The entire complex, or a portion of the complex, such as a lipid portion, can be formulated into liposomes, for example using the method of reverse evaporation, which is well known in the art. Alternatively the lipid portion of the complex or the entire complex, can be formulated by other well known methods for liposome formation such as sonication or microfluidization. These liposome formulations are effective for transfecting DNA into cultured cells.

In one embodiment, a complex containing the fusogenic peptide or protein and the nucleic acid (where the fusogenic peptide or protein can be conjugated to a nucleic-acid binding group) is first formed and then combined with a cationic lipid for transfection. In a related embodiment, a peptide- or protein-lipid conjugate is combined optionally with other lipids, including any appropriate cationic lipid, and then combined with nucleic acid for transfection. In another related embodiment, a nucleic acid-lipid complex is formed and then combined with a fusogenic peptide or protein for transfection. As discussed above, the lipid-containing complexes of any of these embodiments can be liposomal or non-liposomal formulations.

The complexes and methods of the present invention, especially those involving transfection compositions that include complexes provided herein, can be used for in vitro and in vivo transfection of cells, particularly of eukaryotic cells, and more particularly to transfection of higher eukaryotic cells, including animal cells. The methods of this invention can be used to generate transfected cells which express useful gene products. For example, the methods can be used to produce recombinant antibody molecules, typically by expressing a recombinant light chain molecule and a recombinant heavy chain molecule from one or more expression vectors that are introduced into a cell, especially a suspension cell, using the complexes provided herein. The methods of this invention can also be employed as a step in the production of transgenic animals. The methods of this invention are useful as a step in any therapeutic method requiring introduction of nucleic acids into cells including methods of gene therapy and viral inhibition and for introduction of antisense or antigene nucleic acids, ribozymes, RNA regulatory sequences, siRNA, RNAi, Stealth™ RNAi (Invitrogen Corporation, Carlsbad Calif.) or related inhibitory or regulatory nucleic acids into cells. In particular, these methods are useful in cancer treatment, in in vivo and ex vivo gene therapy, and in diagnostic methods.

The transfection compositions and methods of this invention comprising peptides, proteins, peptide or protein fragments or modified peptides or modified proteins, can also be employed as research agents in any transfection of eukaryotic cells done for research purposes.

Accordingly, provided herein is a method of introducing a macromolecule into a cell, that includes forming a transfection composition that includes a nucleic acid and a complex comprising a lipid of Formula (I) and a fusion agent, wherein the fusion agent includes a fusion promoting amino acid sequence derived from a fusion protein of a non-enveloped virus; and contacting a eukaryotic cell with the transfection composition. Provided in the Examples section herein are illustrative protocols for using compositions of the present invention to transfect eukaryotic cells. As disclosed herein, the fusion agent in illustrative examples is a fusion peptide derived from the FAST protein of a Reovirus, most preferably a fusion peptide that is between 5 and 50 amino acids in length wherein at least 10 contiguous amino acids of the fusion peptide are at least 75, 80, 85, 90, 95 or 100% identical to a hydrophobic region of a Reovirus FAST protein, and a polycationic peptide sequence.

It will be understood that quantities, concentrations and volumes of complexes, complex components, and nucleic acid or other macromolecules, incubation times, mixing protocols, and other specific aspects of the methods of the invention are known in the art or can be optimized and/or identified using methods known in the art. As illustrated in the Examples section herein, volumes and concentrations of nucleic acid or other macromolecule, volume and concentration of the transfection complexes provided herein, volumes and compositions of diluents, and volume and concentration of cells, can be determined using standard experimental approaches for such optimization and titration, including, for example, methods that utilize cytotoxicity assays and/or methods that employ transfection using nucleic acid expression vectors that express reporter genes, such as beta galactosidase, luciferase, and/or fluorescent proteins. Furthermore, cell densities can be optimized using standard methods, and cell densities for transfections using the transfection complexes provided herein can range, for example, from high density >75% to low density <50%

Exemplary diluents for complex formation, for example, include reduced serum, or serum-free media, such as D-MEM and RPMI 1640 and OptiPro™, Opti-MEM® (Invitrogen Corporation). Incubation times for forming complexes can be determined using routine methods, although typical incubation times are between 5 and 240 minutes. In addition, it will be understood that media for cell culturing can be chosen based on the cell line to be transfected and based on the particular application of the method. For example, for the production of proteins in suspension cells, in illustrative embodiments, reduced serum, and preferably serum-free medium can be used. In certain illustrative embodiments, animal original free medium is employed, such as, but not limited to, 293 Expression Medium (Invitrogen Corporation) and CD-CHO Medium (Invitrogen Corporation). In certain aspects depending on the cell type to be transfected, antibiotics can be excluded from post-transfection media. Incubation times for post-transfection culturing of cells varies depending, but typically ranges from 2 hours to 7 days. For large-scale protein production, cells can be incubated, as a non-limiting example, for between 1 day and 7 days.

It will be understood that a wide range of concentrations of lipids of Formula (I), co-lipids and transfection enhancing agents can be used in the complexes, compositions and methods provided herein. For example, in an illustrative non-limiting example of a composition provided herein that includes a complex of a lipid of Formula (I) and a fusogenic peptide, the total exemplary, non-limiting combined concentration of lipid of Formula (I) and fusogenic peptide in the composition can be between 1 mg/ml and 4 mg/ml. The range of peptide added to the lima at 1 mg/ml can be between 100 µgml and 3 mg/ml. the ratio of the helper lipid to cationic lipid can be between 0.25:1.0 (molar) and pure compound Cells that can be transfected according to the present invention include, for example, virtually any eukaryotic cell including primary cells, cells in culture, and cells in cultured tissue. The cells can be attached cells or cells in suspensions. In certain illustrative aspects, the cells are suspension CHO-S cells and suspension 293-F cells. Other cells that can be transfected using the agents and methods of the invention include, but are not limited to, 293, such as GripTite 293 MSR (Invitrogen Corporation), CHO, Cos7, NIH3T3, Hela, primary fibroblast, A549, Be2C, SW480, Caco2, primary neurons. Jurkat, C6, THP1, IMR90, HeLa, ChoK1, GT293, MCF7, HT1080, LnCap, HepG2, PC12, SKBR3, and K562 cells.

In another embodiment, provided herein is a method for producing a protein comprising, transfecting a cell with a nucleic acid molecule encoding the protein, incubating the cell to produce the protein, and collecting the protein, wherein the transfecting is performed by contacting the cell with a transfection composition of the present invention. The composition for transfecting the cell can be any of the compositions provided herein. By way of example, such compositions can include the nucleic acid molecule encoding the protein, a fusion agent, and a lipid if Formula (I), wherein the fusion agent include a fusion promoting amino acid sequence derived from a fusion protein of a non-enveloped virus, such as a reovirus protein.

Pharmaceutical Compositions

Transfection agents and transfection-enhancing agents of this invention can be provided in a variety of pharmaceutical compositions and dosage forms for therapeutic applications. For example, injectable formulations, intranasal formulations and formulations for intravenous and/or intralesional administration containing these complexes can be used therapy.

In general the pharmaceutical compositions of this invention should contain sufficient transfection agent and any enhancing agents (peptide, protein, etc.) to provide for introduction of a sufficiently high enough level of nucleic acid into the target cell or target tissue such that the nucleic acid has the desired therapeutic effect therein. The level of nucleic acid in the target cell or tissue that will be therapeutically effective will depend on the efficiency of inhibition or other biological function and on the number of sites the nucleic acid must affect.

The dosage of transfection compositions described herein administered to a patient will depend on a number of other factors including the method and site of administration, patient age, weight and condition. Those of ordinary skill in the art can readily adjust dosages for a given type of administration, a given patient and for a given therapeutic application.

It will be appreciated by those of ordinary skill in the art that the transfection composition should contain minimal amounts of inhibitory components, such as serum or high salt levels, which may inhibit introduction of nucleic acid into the cell, or otherwise interfere with transfection or nucleic acid complexation. It will also be appreciated that any pharmaceutical or therapeutic compositions, dependent upon the particular application, should contain minimal amounts of components that might cause detrimental side-effects in a patient.

The transfection compositions described herein may be formulated into compositions which include a pharmaceutically active agent and a pharmaceutically acceptable diluents, excipients or carriers therefor. Such compositions may be in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in Remington's Pharmaceutical Sciences, (Gennaro, ed., Mack Publishing Co., Easton Pa., 1990, herein incorporated by reference).

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. When the carrier serves as a diluent, it may be a solid, semi-solid or liquid material which acts as a vehicle, excipient or medium for the active ingredient. In the case of injections, it is possible to prepare solutions or liposomes of one or more lipids of the present invention in pharmaceutically acceptable carriers such as an aqueous or non-aqueous solvent. Examples of solvents which may be used are distilled water for injection, physiological saline solution, Ringer's solution, plant oil, synthetic fatty acid glycerides, higher fatty acid esters, propylene glycol, and the like.

Reagent Kits

Components of the transfection compositions of this invention can be provided in a reagent kit. The kit may contain a transfection agent and an amino acid sequence from a fusogenic protein of a non enveloped virus. This kit can also include a transfection enhancing agent such as a transfection-enhancing peptide, protein or fragment thereof or a transfection enhancing compound. The transfection agent, the amino acid sequence, typically a fusogenic peptide, and the transfection enhancing agent, when present, can each be included as a mixture (i.e. in a single container, typically a tube and/or vial), or can be included as separate portions (i.e. in separate containers, for example separate vials and/or tubes). The kits of the present invention, as will be understood, typically include vessels, such as vials and/or tubes, that are packaged together, for example in a cardboard box. The kits can be shipped from a supplier to a customer. For example, in one example provided herein is a kit that includes a vial that includes a liposomal formulation that includes a transfection agent and a transfection enhancing peptide. The kit can also include, for example, a separate vessel that includes a transfection enhancing agent, such as a transfection enhancing peptide, for example Plus Reagent™ (Invitrogen Corp., Carlsbad, Calif.). The kit can also include in separate containers, cells, cell culture medium, and a reporter nucleic acid sequence, such as a plasmid that expresses a reporter gene. In certain examples, the culture medium can be reduced-serum medium and/or protein expression medium.

In one embodiment, a kit comprises individual portions of, or a mixture of, cationic lipid, such as a lipid of Formula I, and peptide, protein or fragment thereof or modified peptide, protein or fragment thereof. In another embodiment, a kit comprises individual portions of or a mixture of, polycationic polymers and peptide, protein or fragments thereof or modified peptide, protein or fragments thereof. Cationic lipid transfection kits can optionally include neutral lipid as well as other transfection-enhancing agents or other additives, and the relative amounts of components in the kit may be adjusted to facilitate preparation of transfection compositions. Kit components can include appropriate medium or solvents for other kit components.

Cationic lipid transfection kits comprising a monocationic or polycationic lipid composition, such as a lipid of Formula I, and further including a neutral lipid and a modified peptide or protein are preferred. Dendrimer transfection kits can optionally include other transfection enhancing agents, such as DEAE-dextran and/or chloroquine, as well as other additives and the relative amounts of components in the kit may be adjusted to facilitate preparation of transfection compositions. Kits provided by this invention include those comprising an individual portion of a polycationic lipid composition comprising DOSPA and DOPE or a monocationic lipid composition comprising DOTMA and DOPE and a portion of modified peptide, particularly a spermine-modified peptide. Kits provided by this invention include those comprising an individual portion of a polycationic polymer and a portion of a spermine-modified peptide.

In related embodiments, kits of this invention can comprise a peptide- or protein-lipid conjugate or a peptide- or protein-polycationic polymer conjugate in combination with non-conjugated lipids, non-conjugated polycationic polymer and other agents to facilitate transfection.

Kits of this invention can include those useful in diagnostic methods, e.g., diagnostic kits which in addition to transfection agent and transfection-enhancing agents (e.g., proteins, peptides, and fragments and modifications of peptides and proteins) can contain a diagnostic nucleic acid. A diagnostic nucleic acid is a general term for any nucleic acid which can be employed to detect the presence of another substance (most generally an analyte) in a cell. For example, when transfected into a cell a diagnostic nucleic acid may increase or decrease expression of a gene therein in response to the presence of another substance in the cell (e.g., a protein, small molecule, steroid, hormone, or another nucleic acid). Diagnostic nucleic acids also include those nucleic acids that carry some label or otherwise detectable marker to a particular target cell or target tissue for detection of the target cell or tissue or for detection of a substance in the target cell or tissue.

Nucleic acids that can be transfected by the methods of this invention include DNA and RNA of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Therapeutic nucleic acids include those nucleic acids that encode or can express therapeutically useful proteins, peptides or polypeptides in cells, those which inhibit undesired expression of nucleic acids in cells, those which inhibit undesired enzymatic activity or activate desired enzymes in cells.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

The lipids of Formula I can be used as the cationic lipid(s) of the kits described above, and may independently be provided in a reagent kit. In general, the kit contains a lipid of Formula (I) in a suitable container. The lipid may be, for example, in a solution of an organic solvent, such as ethanol, in a buffer, or in a solvent/buffer mixture In addition, the kit may include, but is not limited to, a lipid of Formula (I), and an amino acid sequence from a fusogenic protein of a non enveloped virus in a suitable solvent or buffer.

In one embodiment, a kit may comprise individual portions of, or a mixture of, lipids of Formula (I) and peptide, protein or fragment thereof or modified peptide, protein or fragment thereof. Kits which include lipids of Formula (I) can optionally include neutral lipid as well as other transfection-enhancing agents or other additives, and the relative amounts of components in the kit may be adjusted to facilitate preparation of transfection compositions. Kit components can include appropriate medium or solvents for other kit components.

Kits which include lipids of Formula (I), a neutral lipid and a modified peptide or protein are preferred. Kits provided by this invention include those composition comprising an individual portion of a lipid of Formula (I), DOPE and a portion of modified peptide, particularly a spermine-modified peptide. Kits provided by this invention include those comprising an individual portion of a lipid of Formula (I), and a portion of a modified peptide containing a stretch of basic amino acids such lysine, ornithine, or arginine.

Methods for Selling

Also provided is a method for selling a fusogenic peptide, lipid, transfection complex, transfection composition, and/or kit provided herein, comprising presenting to a customer an identifier that identifies the fusogenic peptide, lipid, complex and/or transfection composition, and/or a kit provided herein, and providing access to the customer to a purchase function for purchasing the fusogenic peptide, lipid, transfection complex, transfection composition, and/or kit provided herein using the identifier. The identifier is typically presented to the customer as part of an ordering system. The ordering system can include an input function for identifying a desired product, and a purchasing function for purchasing a desired product that is identified. The ordering system is typically under the direct or indirect control of a provider. A customer as used herein, refers to any individual, institution, corporation, university, or organization seeking to obtain biological research products and services. A provider as used herein, refers to any individual, institution, corporation, university, or organization seeking to provide biological research products and services.

The present invention also provides a method for selling a fusogenic peptide, lipid, transfection complex, transfection composition, and/or kit provided herein, comprising: presenting to a customer an input function of a telephonic ordering system, and/or presenting to a customer a data entry field or selectable list of entries as part of a computer system, wherein the fusogenic peptide, lipid, transfection complex, transfection composition and/or kit is identified using the input function. Where the input function is part of a computer system, such as displayed on one or more pages of an Internet site, the customer is typically presented with an on-line purchasing function, such as an online shopping cart, wherein the purchasing function is used by the customer to purchase the identified fusogenic peptide, lipid, transfection complex, transfection composition, and/or kit. In one aspect, a plurality of identifiers are provided to a customer, each identifying a different fusogenic peptide, lipid, complex and/or transfection composition, and/or a kit provided herein, or a different volume or weight of the fusogenic peptide, lipid, complex and/or transfection composition, and/or a kit provided herein. The method may further comprise activating the purchasing function to purchase the lipid, transfection complex, transfection composition, and/or kit provided herein. The method may still further comprise shipping the purchased fusogenic peptide, lipid, transfection complex, transfection composition, and/or kit provided herein to the customer. The fusogenic peptide, lipid, transfection complex, transfection composition, and/or kit can be shipped by a provider to the customer. The provider typically controls the input function, and can control the web site accessed to access the input function to purchase a fusogenic peptide, lipid, complex and/or transfection composition, and/or a kit provided herein.

The present invention, thus generally described, will be understood more readily by reference to the following examples, which are provided by way of illustration and are not intended to be limiting of the present invention.

EXAMPLES

Example 1

"After" Transfection Protocol where Peptide is Added to DNA/Lipid Complex

Transfection of CHO-K1, NIH3T3, A549, Cos-7 and BE(2)C with β-galactosidase reporter plasmid pCMV•SPORT-β-gal was carried out as follows:

Cells were plated in a 96-well plates with 100 µl of media containing 10% fetal calf serum the day before transfection such that a desired confluency (70%-95%) was achieved. The following day a transfection agent that includes a liposomal composition of the lipid DMTS (Dimyrstyl-tetrahydroxyspermine) and DOPE (2:1 DMTS:DOPE) and DNA were mixed in Opti-MEM to form DNA/lipid complexes. Complexes were formed by adding various amounts of lipids (0.1 to 0.35 µl) to 100 µl of Opti-MEM. DNA (100 ng) was added to 100 µl Opti-MEM. The DNA and lipid solutions were then mixed to form DNA lipid complexes. The complexes were incubated for at least 15 minutes after which added to the DNA lipid complexes, was 20 µl of various amounts of a peptide having the sequence of a Prototypical Avian reovirus fusogenic peptide provided herein, as follows:

(SEQ ID NO: 28)
Arg-Met-Pro-Pro-Gly-Ser-Cys-Asn-Gly-Ala-Thr-Ala-

Val-Phe-Gly-Asn-Val-His-Lys-Lys-Lys-Lys-Lys-Lys-

Lys-Lys-Lys-Lys-Lys-Lys-Lys-Lys-Lys-Lys, and incubated for 15 minutes to form a DNA/lipid/peptide complex. After incubation of 30 minutes, 20 µl of DNA/lipid/peptide complex was added directly to the cells in 10% serum. Cells were incubated for an additional 24 hours to allow expression of the plasmid. Medium was removed and the cells were lysed in 100-200 µl of lysis buffer. The lysates (20 µl) were assayed for β-gal activity using the enzymatic substrate ONPG. Total activity was determined by reading the OD at 405 using Bio-Rad Benchmark Microplate Spectrophotometer.

Example 2

"Before" Transfection Protocol where Peptide is Mixed with DNA and Added to Lipid to Form Complex Transfection of CHO-K1, NIH3T3, A549, Cos-7 and BE(2)C with β-galactosidase reporter plasmid pCMV•SPORT-β-gal was carried out as follows:

Cells were plated in 96-well plates with 100 µl of media containing 10% fetal calf serum the day before transfection such that a desired confluency (70%-95%) was achieved. The following day a transfection agent that includes a liposomal composition of the lipid DMTS (Dimyrstyl-tetrahydroxyspermine) and DOPE (2:1 DMTS:DOPE) and DNA/peptide were mixed in Opti-MEM to form DNA/lipid/peptide complexes. The peptide and DNA were mixed for 15 minutes and the mixed with lipid for an addition 15 minutes Complexes were formed by adding various amounts of lipids (0.1 to 0.35 µl) to 100 µl of Opti-MEM. DNA (100 ng) was added to 100 µl Opti-MEM then various amounts of peptide having the sequence of Prototypical Avian reovirus fusogenic peptides provided herein, as follows:

Arg-Met-Pro-Pro-Gly-Ser-Cys-Asn-Gly-Ala-Thr-Ala-

Val-Phe-Gly-Asn-Val-His-Lys-Lys-Lys-Lys-Lys-Lys-

Lys-Lys-Lys-Lys-Lys-Lys-Lys-Lys-Lys-Lys were added to the DNA mixture and incubated for 15 minutes. The DNA/peptide and lipids solutions were then mixed to form DNA lipid complexes. The complexes were incubated for an additional 15 minutes. After incubation, 20 µl of complexes were added directly to the cells in 10% serum. Cells were incubated for an additional 24 hours to allow expression of the plasmid. Medium was removed and the cells were lysed in 100-200 µl of lysis buffer. The lysates (20 µl) were assayed for β-gal activity using the enzymatic substrate ONPG. Total activity was determined by reading the OD at 405 using Bio-Rad Benchmark Microplate Spectrophotometer.

Figure 2:
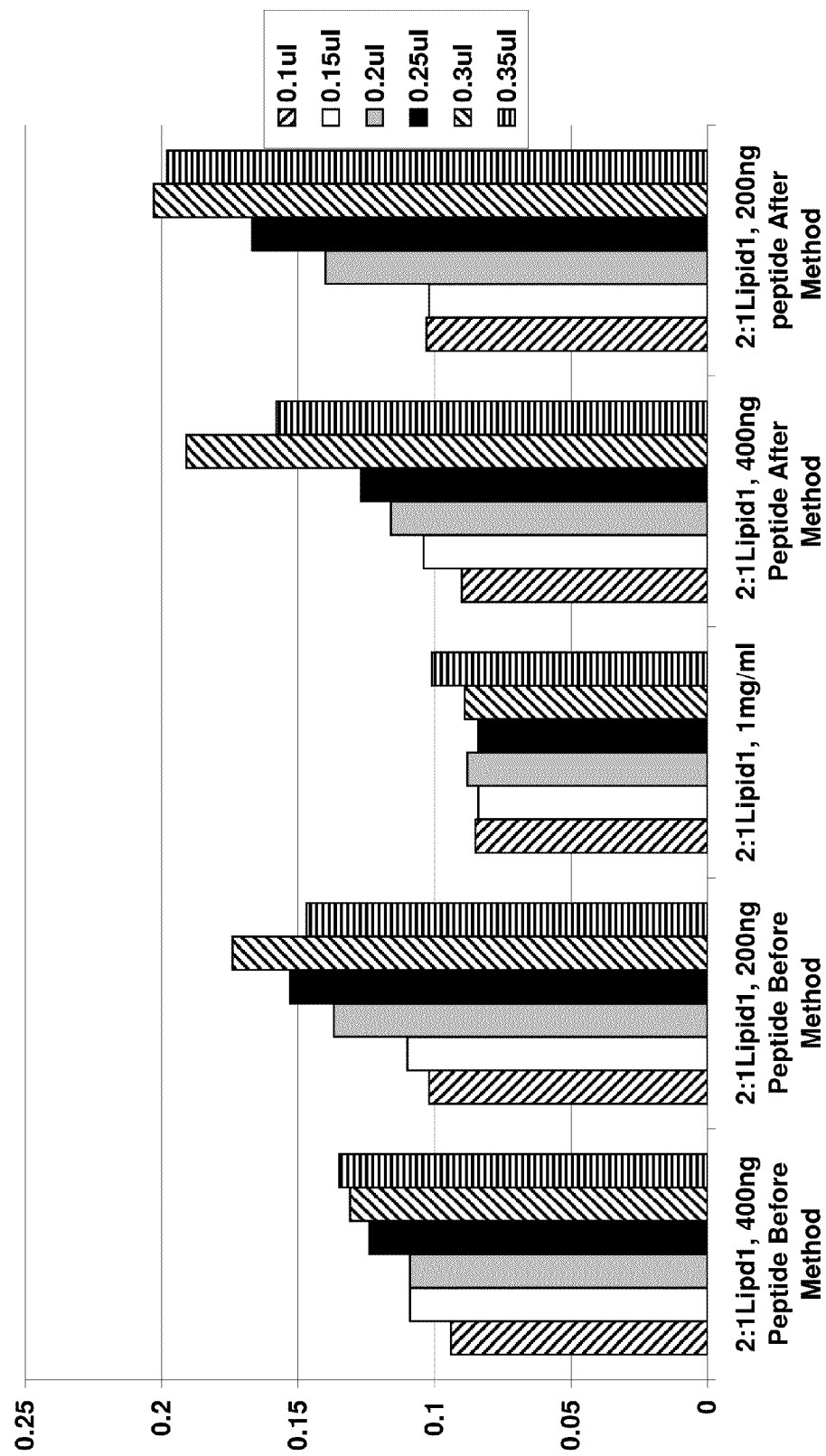
FIG. 2 shows the results of transfection of NIH-3T3 cells using the complexes of the invention using "before" and "after" protocols.
Figure 3:
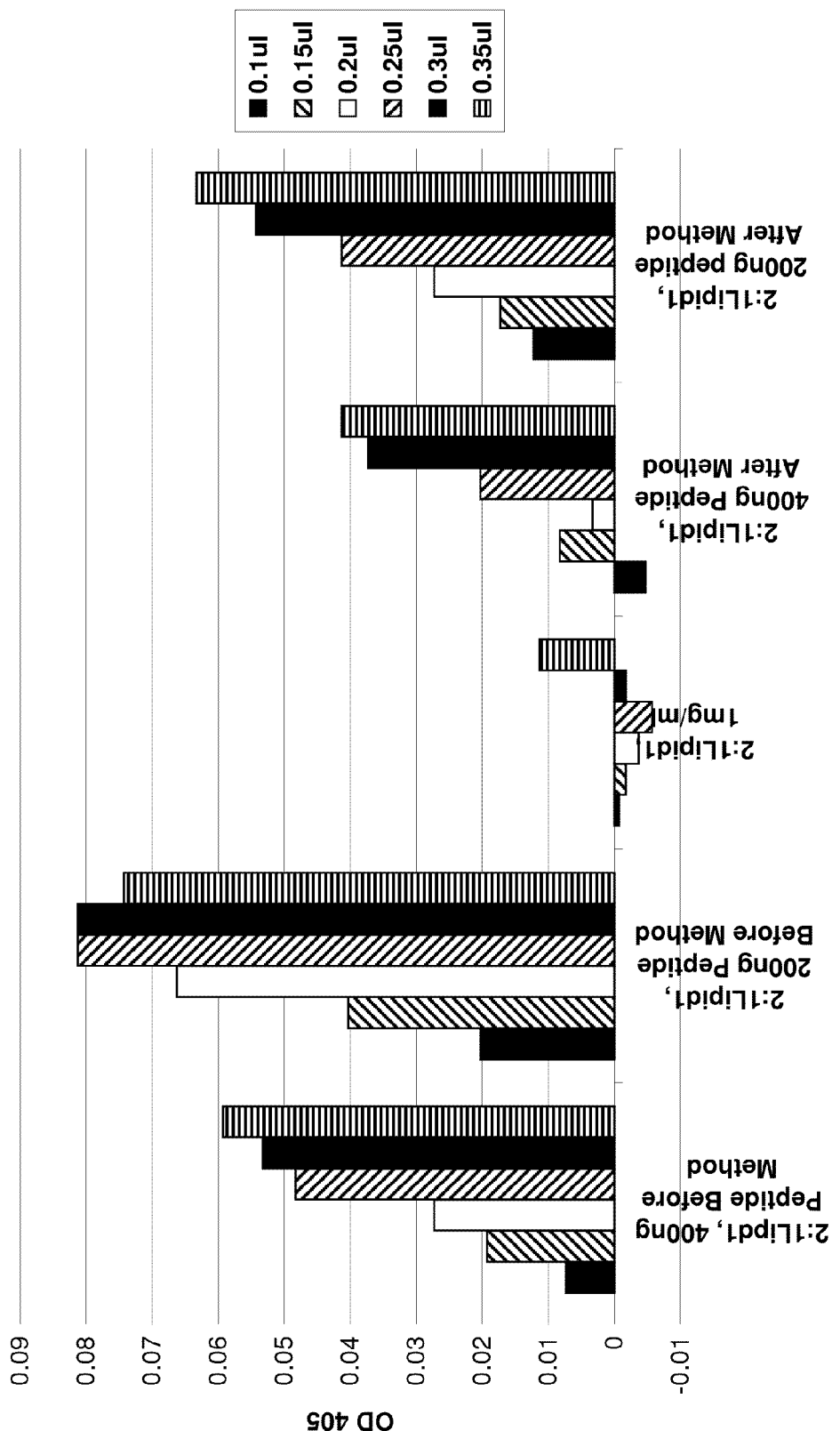
FIG. 3 shows the results of transfection of A549 cells using the complexes of the invention using "before" and "after" protocols.
Figure 4:
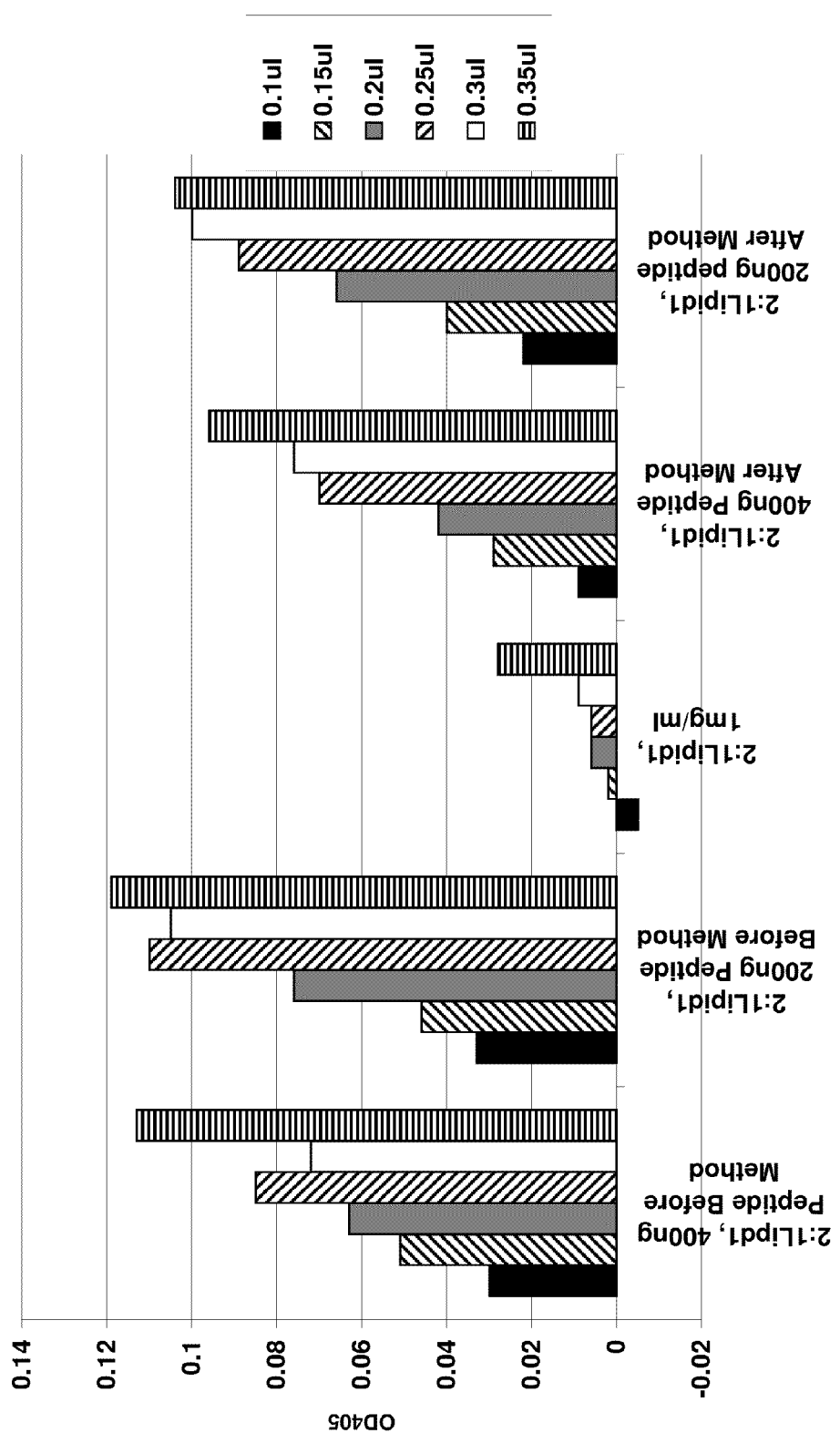
FIG. 4 shows the results of transfection of COS cells using the complexes of the invention using "before" and "after" protocols.
Figure 5:
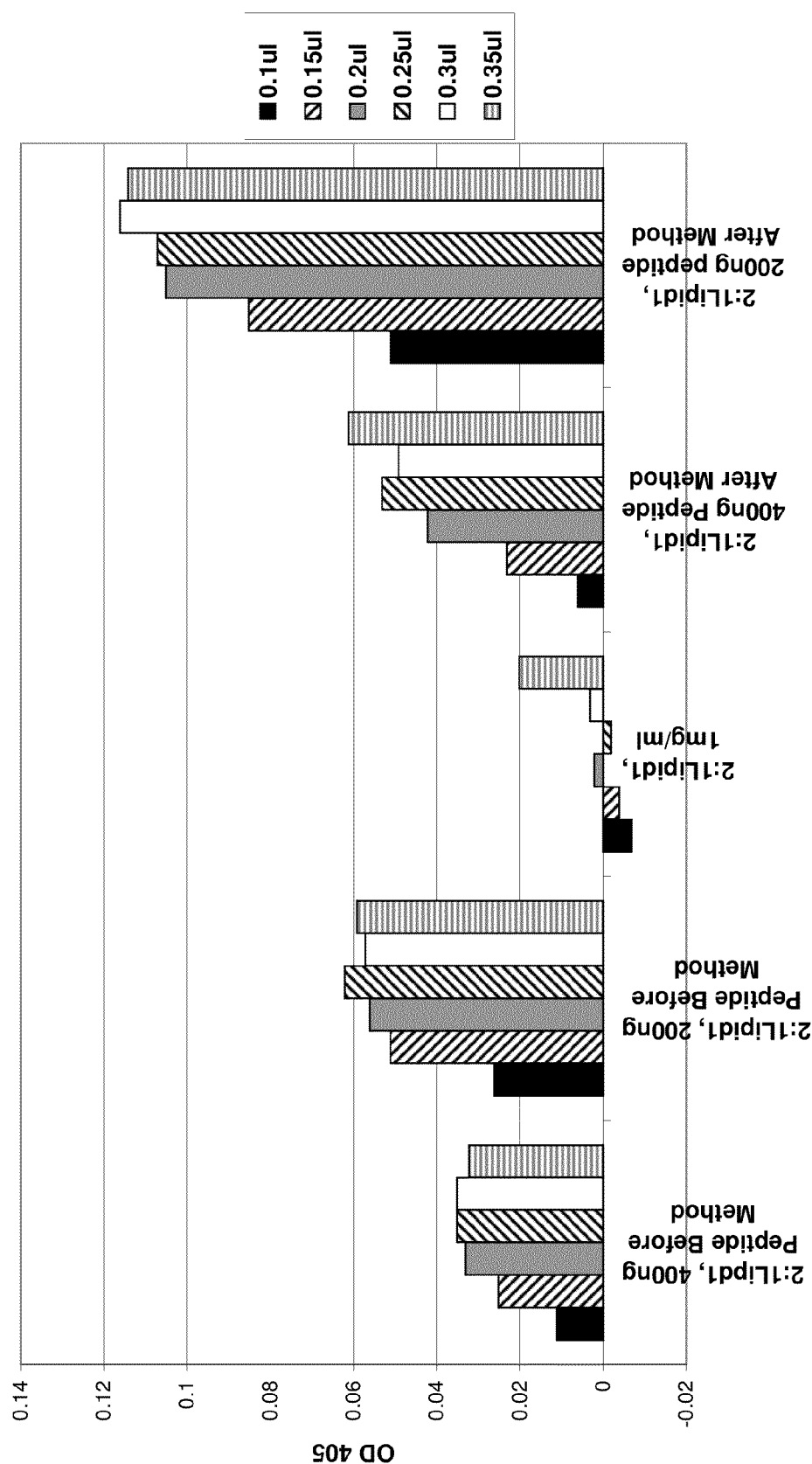
FIG. 5 shows the results of transfection of BE2C cells using the complexes of the invention using "before" and "after" protocols.

In all examples, as shown in FIG. 1-5, the addition of the peptide to the DNA and then adding cationic lipid or adding peptide to the DNA/lipid complex gave enhancement of transfection and reduced the amount of lipid required to enhance transfection. For optimal results, the choice of whether to use the before or after transfection method will depend on the nature of the cell line that is being transfected. Other lipids such as DMRIE-C, LIPOFECTAMINE™, and Fugene6 were found to be enhanced by addition of the peptide using the before method Example 3

Exemplary Transfection Protocol for Cells in Suspension

Transfection of CHO-S and HEK293 in suspension with β-galactosidase reporter plasmid pCMV•SPORT-β-gal is carried out as described below.

Prior to transfection the cells are cultivated in suspension in a humidified 37° C. and 8% $CO_2$ on an orbital shaker. Antibiotics are not added to the media as this may cause cell death. In addition clumping can lower transfection efficiency therefore the cells are sufficiently agitated at regular intervals to avoid clumping and anti-clumping agents are not added during culturing and prior to transfection. However, anti-clumping agents are optionally used post-transfection.

A) For routine culturing of HEK293 cells, shake at 135-155 rpm keeping the cell densities between 0.1 and $2 \times 10^6$ cells/mL of culture. A cell density above $2 \times 10^6$ cells/mL will result in a loss of transfection efficiency.

B) For routine culturing of CHO-S cells, shake at 120-135 rpm keeping the cell densities between 0.05 and $1.5 \times 10^6$ cells/mL of culture. A cell density above $1.5 \times 10^6$ cells/mL will result in a loss of transfection efficiency. The media is supplemented with L-glutamine to a final concentration 8 mM.

Approximately 24 hours before transfection, CHO-S cells (at $5-6 \times 10^5$ cells/ml) or HEK293 cells (at $6-7 \times 10^5$ cells/mL), are placed in a flask on an orbital shaker platform rotating at 135-155 rpm at (HEK293 cells) or at 120-135 rpm at (CHO-S cells) at 37° C. and 8% $CO_2$ and allowed to continue to cultivate. The following day, the cells are diluted to about $1 \times 10^6$ cells/ml and then 30 mL of the diluted cells are placed into a 125 mL shake flask. Then in a tube 30 μg of plasmid DNA is mixed with Opti-Pro™ SFM medium to a total volume of 0.6 mL, and in a separate tube 30 μL of a transfection composition provided herein at 2 mg/ml total concentration of fusogenic peptide of Example 1, neutral lipid, and cationic lipid is mixed with Opti-Pro™ SFM medium to a total volume of 0.6 mL. The transfection composition solution is then added to the diluted DNA solution giving a total volume of 1.2 mL. This mixture is then incubated 10 minutes at room temperature to allow the DNA-lipid-fusogenic complex to form. The solution (1.2 mL) of DNA-lipid-fusogenic peptide complex is then slowly added to the 125 mL flask containing the cells while gently swirling the flask.

The transfected cell culture is incubated at 37° C. and 8% $CO_2$ on an orbital shaker platform rotating at 135-155 rpm for an additional 24 hours to allow expression of the plasmid. Medium is removed and the cells are lysed in 100-200 μl of lysis buffer. The lysates (20 μl) are assayed for β-gal activity using the enzymatic substrate ONPG. Total activity is determined by reading the OD at 405 nm using a Bio-Rad Benchmark Microplate Spectrophotometer. Protein expression can be detected within 4 to 8 hours, with maximal protein yield usually between 1-7 days post transfection. This method was successfully employed to transfect cells and express proteins.

Optimizing Protein Expression

To optimize protein expression a time course is obtained between days 1 and 7 post transfection and the peak of protein production is obtained and cell viability is monitored. To assess transfection efficiency via expression of a GFP-type fluorescent protein the culture is monitored starting 24 hours post transfection. For secreted IgG protein production the peak yields are at 5-7 days post transfection.

Scaling Up or Down Transfections

For different culture volumes the following parameters are used:

| Cells | Culture Volume (mL) | Culture Flask (mL) | Rotation Speed (rpm) | Dilution Volume (mL) | DNA quantity (μg) | Transfection composition (μL) | Complex time (min.) |
|---|---|---|---|---|---|---|---|
| CHO—S or HEK293 | 30 | 125 | 135 | 1.2 (2 × 0.6 mL) | 30 | 30 | 10-20 |
| | 30 | 125 | 135 | 1.2 (2 × 0.6 mL) | 30 | 30 | 10-20 |
| CHO—S or HEK293 | 200 | 500 | 135 | 8 (2 × 4 mL) | 200 | 200 | 10-20 |
| | 200 | 500 | 135 | 8 (2 × 4 mL) | 200 | 200 | 10-20 |
| CHO—S or HEK293 | 400 | 1000 | 135 | 16 (2 × 8 mL) | 400 | 400 | 10-20 |
| | 400 | 1000 | 135 | 16 (2 × 8 mL) | 400 | 400 | 10-20 |
| CHO—S or HEK293 | 1000 | 3000 | 70 | 40 (2 × 20 mL) | 1.25 | 1.25 | 20 |
| | 1000 | 3000 | ≤135 | 40 (2 × 20 mL) | 1.0 | 1.0 | 10-20 |

Note: The lipid is tested for absence of microbial contamination using blood agar plates, Sabraud dextrose agar plates and fluid thioglycolate medium and functionally by transfection with a reporter plasmid.

Example 4

Single Tube Protocol

The following protocol is used to transfect DNA (β-galactosidase reporter plasmid pCMV•SPORT-β-gal) into mammalian cells in a 24-well format. The amounts used are on a per well basis.

Adherent Cells

One day before transfection, plate cells in 500 μL of growth medium so that the cells are 50-80% confluent at the time of transfection.

Suspension Cells

Just prior to preparation of the complexes, 200,000-500,000 cells are plated in 500 μL of growth medium.

Transfection

For each transfection sample the complexes are prepared as follows.

500 ng of plasmid DNA is diluted in 100 μL Opti-MEM® I Reduced Serum Medium without serum and is gently mixed.

(For optional transfections with Plus™ Reagent (Invitrogen Inc., Carlsbad Calif.), the Plus™ Reagent is mixed gently and 0.5 μL is added directly to the diluted DNA, and incubated for 5 minutes at room temperature.) Then 1.25 μL of a transfection composition provided herein that includes a fusogenic peptide, a cationic lipid, and a helper lipid is added to the diluted DNA solution (with or without Plus™ Reagent) and the mixture is gently mixed and is incubated for 30 minutes at room temperature to form the complexes. Then approximately 100 μL of the complex is added directly to a well containing the cells and the plate is gently rocked back and forth. Cells are incubated at 37° C. in a $CO_2$ incubator for an additional 24 hours to allow expression of the plasmid. Medium is optionally changed after 4-6 hours.

Medium is removed and the cells are lysed in 100-200 μl of lysis buffer. The lysates (20 μl) are assayed for β-gal activity using the enzymatic substrate ONPG. Total activity was determined by reading the OD at 405 nm using a Bio-Rad Benchmark Microplate Spectrophotometer.

Optimizing Transfections

To obtain the highest transfection performance, the amounts of DNA and lipid are varied as follows for a 24-well format (for other formats, the amounts are adjusted accordingly.)

| Cells | DNA (ng) | Transfection composition (μL) | Optional Plus ™ Reagent (μL) |
|---|---|---|---|
| Sensitive cells (HeLa, HT1080) | 250 | 0.375-1.25 | 1.25-0.5 |
| Most cell lines | 500 | 0.75-3.0 | 0.25-1.0 |
|  | 700 | 1.125-4.5 | 0.375-1.5 |
| Suspension cells And Robust cells (e.g. Jurkat, THP1 and HL60) | 1000 | 1.5-5.0 | 0.5-2.0 |

Generating Stable Cells Lines

Cells are passed at 1:10 (or higher dilution) into fresh medium 1 day after transfection. Selective medium is optionally added the next day.

Scaling Up or DownTransfections

For different culture volumes the following parameters are used:

| Culture Vessel | Surface area per well ($cm^2$) | Volume plating medium (μL) | Dilution Volume (μL) | DNA quantity (ng) | Transfection composition (μL) | Optional Plus ™ Reagent (μL) |
|---|---|---|---|---|---|---|
| 96-well | 0.3 | 100 | 20 | 100 | 0.25 | 0.1 |
| 48-well | 1.0 | 200 | 40 | 200 | 0.5 | 0.2 |
| 24-well | 2 | 500 | 100 | 500 | 1.25 | 0.5 |
| 12-well | 4 | 1000 | 200 | 1000 | 2.5 | 1.0 |
| 6-well | 10 | 2000 | 500 | 2500 | 6.25 | 2.5 |

Reverse Transfection

Rapid 96-well transfections are obtained by plating cells directly into the transfection mix. Complexes are prepared in the plate and cells are directly added at twice the cell density as described above, in 100 μL volume. More lipid is used for optimal transfection.

Note: The transfection composition is tested for absence of microbial contamination using blood agar plates, Sabraud dextrose agar plates and fluid thioglycolate medium and functionally by transfection with a reporter plasmid.

Example 5

High-Throughput Protocol

The following protocol is used to transfect DNA (β-galactosidase reporter plasmid pCMV•SPORT-β-gal) into mammalian cells for higher throughput or for using smaller amounts of transfection composition. In this procedure, the reagents are pre-diluted first, and then a larger volume is added to the diluted DNA. The amounts used are on a per well basis for a 96-well format.

Adherent Cells

One day before transfection, plate cells in 100 μL of growth medium so that the cells are 50-80% confluent at the time of transfection.

Suspension Cells

Just prior to preparation of the complexes, 40,000-100,000 cells are plated in 100 μL of growth medium.

Transfection

For each transfection sample the complexes are prepared as follows.

100 ng of plasmid DNA is diluted in 10 μL Opti-MEM® I Reduced Serum Medium without serum and is gently mixed. (For optional transfections with Plus™ Reagent (Invitrogen Inc., Carlsbad Calif.), the Plus™ Reagent is mixed gently, diluted 10 fold with Opti-MEM® I Reduced Serum Medium without serum (0.1 μL per well), and 1 μL of diluted Plus™ Reagent is added directly to the diluted DNA, is mixed gently and is incubated for 5 minutes at room temperature.) Then a stock solution of transfection composition is made by diluting 0.25 μL per well of a transfection composition provided herein that includes a fusogenic peptide, a cationic lipid, and a neutral lipid at a combined total concentration of 1 mg/ml- to 2 mg/ml in Opti-MEM® I Reduced Serum Medium without serum to give 10 μL per well. Then 10 μL of a diluted a transfection composition provided herein that includes a fusogenic peptide, a neutral lipid, and a cationic lipid is added to the diluted DNA solution (with or without Plus™ Reagent) and the mixture is gently mixed and is incubated for 30 minutes at room temperature to form the complexes. Then approximately 20 μL of the complex is added directly to each well containing the cells and the plate is gently rocked back and forth. Cells are incubated at 37° C. in a $CO_2$ incubator for an additional 18-48 hours prior to a test for transgene expression. Medium is optionally changed after 4-6 hours.

Medium is removed and the cells are lysed in 100-200 μl of lysis buffer. The lysates (20 μl) are assayed for β-gal activity using the enzymatic substrate ONPG. Total activity was determined by reading the OD at 405 nm using a Bio-Rad Benchmark Microplate Spectrophotometer.

For Optimizing Transfections, Generating Stable Cells Lines and Scaling Up or DownTransfections see Example 4.

All compounds in the Examples below were characterized by mass spectrometry and the mass spectra conformed to the expected formulae.

Example 6

Synthesis of 1,4-Bis[(3-(3-aminopropyl)-oleoylamino)-2-hydroxypropyl]piperazine piperazine (2.0 g), N-(2,3-epoxypropyl)phthalmide (12.0 g) and lithium perchlorate (6.4 g) were combined in 300 ml absolute ethanol and heated under reflux for 2 days. The resulting mix was cooled, and the precipitate obtained by filtration was rinsed with ethanol to provide 1,4,-bis(2-hydroxy-3-phthalimidopropyl)piperizine (Compound 1), as an off-white solid (8.5 g, 75% yield).

Hydrazine hydrate (4 ml) was added to a solution of Compound 1 (8.5 g) in 200 ml of ethanol. The reaction mix was heated under reflux overnight and cooled to room temperature for about 1 hr and the precipitate filtered. The precipitate was rinsed with ethanol and used further without purification. The compound that was obtained, 1,4-bis(3-amino-2-hydroxypropyl)piperazine (Compound 2) was acylated using oleoyl chloride followed by reduction with lithium aluminum hydride. To an ice cooled solution of compound 2 in THF (400 ml) was added 15 g of oleoyl chloride and 15 ml of DIPEA. The reaction mix was stirred overnight under reflux. The reaction mixture was diluted with chloroform (400 ml) and sequentially extracted with water (2×200 ml), 10% HCl (300 ml) and 0.2% KOH (200 ml). The organic solvent was removed on a rotary evaporator and the resulting compound dried overnight in vacuo.

The crude diamide compound was suspended in anhydrous THF (400 ml) and 100 ml of a 1M lithium aluminium hydride solution in THF was added drop-wise. After the addition was completed, the reaction mix was refluxed overnight. More THF (150 ml) was added and the reaction mix was cooled to room temperature. A 15% sodium hydroxide solution (200 ml) was added drop-wise to the mixture and stirred for 2 hours. The THF layer was decanted and the remaining suspension was exhaustively extracted with chloroform, using TLC to monitor the presence of the desired product in the chloroform layer. The THF and chloroform layers were combined and evaporated to obtain the desired compound, octadec-9-enyl-{2-hydroxy-3-[4-(3-octadec-9-enylamino-2-hydroxypropyl)-piperazin-1-yl]-propyl}-amine (Compound 3) (3.4 g). The product was characterized by mass spectrometry.

Compound 3 (2.5 g) was treated with N-(3-bromopropyl) phthalimide (2.19 g) and diisopropylethylamine (2 ml) in DMF (10 ml). The reaction mixture was heated at 100° C. for 3 hours and then diluted with chloroform (300 ml) and extracted with water (4×300 ml). The chloroform was removed on a rotary evaporator and the residue subjected to flash chromatography using chloroform and methanol/chloroform as eluants to obtain the desired phthlamide adduct (Compound 4). Hydrazine hydrate (0.75 ml) was added to a solution of the phthalimide compound 4 (1.7 g) in 100% reagent alcohol (100 ml). The reaction mix was refluxed overnight and cooled to room temperature for about 1 hr. The reaction mix was then cooled at 4° C. overnight and the precipitate obtained by filtration. The solid was washed with ethanol chilled to −20° C. (2×20 ml) and dried in vacuo. The residue was dissolved in chloroform (300 ml), filtered and extracted twice with water (200 ml). The chloroform was removed on a rotary evaporator to give 1,4-Bis[(3-(3-aminopropyl)-oleoylamino)-2-hydroxypropyl]piperazine (Compound 5) in a quantitative yield. This material was acidified with HCL in dioxane and purified on reverse phase (C-18) flash chromatography using aqueous methanol as eluant and characterized by TLC and mass spectrometry.

In this manner compounds with alkyl groups varying in length from $C_{12}$ to $C_{18}$ were synthesized. Examples include compounds where $R_1$, $R_2$=H; $X_1$, $X_2$=$CH_2$; $R_4$, $R_5$=$CH_2$—CHOH—$CH_2$; $R_3$, $R_6$=N; $W_1$, $W_2$=H; q, p, m=1; Y=piperazine; and $Z_1$ and $Z_2$ both are palmityl, myristyl; lauryl; or stearyl.

Example 7

Synthesis of 1,4-Bis[(3-(3-amino-2-hydroxypropyl)-oleoylamino)-2-hydroxypropyl]piperazine Compound 3, octadec-9-enyl-{2-hydroxy-3-[4-(3-octadec-9-enylamino-2-hydroxypropyl)-piperazin-1-yl]-propyl}-amine (3.2 g) was dissolved in ethanol (110 ml), and N-(2,3-epoxypropyl)phthalmide (2.3 g) and lithium perchlorate (1.1 g) were added to the reaction mix which was then heated under reflux overnight. The reaction mix was cooled and diluted with chloroform (300 ml) and extracted with water (2×300 ml). The organic phase was concentrated and subjected to flash chromatography using chloroform/methanol (1-3%) as eluant to provide the desired phthalamide (3.05 g)

Hydrazine hydrate (0.7 ml) was added to a solution of the phthalimide (3.0 g) in 100 ml of ethanol. The reaction mix was refluxed overnight and cooled to room temperature for about 1 hr and the precipitate filtered. The filtrate was diluted with chloroform (300 ml) and extracted with water (2×300 ml). The organic layer was concentrated and the material thus obtained with acidified using HCL in dioxane and subjected to flash chromatography on a $C_{18}$ reversed-phase column. The desired compound, 1,4-Bis[(3-(3-amino-2-hydroxypropyl)-oleoylamino)-2-hydroxypropyl]piperazine, was obtained as a solid (2.32 g) ($R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$=oleoyl; $W_1$, $W_2$=OH; q, p, m=1; and Y=piperazine). In this manner compounds with alkyl groups varying in length from $C_{12}$ to $C_{18}$ were synthesized. Examples include compounds where:
$R_1$, $R_2$=H; $X_1$, $X_2$=$CH_2$; $R_4$, $R_5$=$CH_2$—CHOH—$CH_2$; $R_3$, $R_6$=N; $W_1$, $W_2$=OH; q, p, m=1; Y=piperazine; and $Z_1$ and $Z_2$ both are palmityl, myristyl; lauryl; or stearyl.

Example 8

Synthesis of 1,4-Bis[(3-(3-amino-2-hydroxypropyl)-oleoylamino)-propyl]piperazine To an ice cooled solution of 1,4-bis(3-aminopropyl)piperazine (10.0 g) in THF (200 ml) was added 38 g of technical oleoyl chloride (85%). The reaction mix was stirred overnight at room temperature. The reaction mixture was diluted with chloroform (500 ml) and extracted with saturated sodium bicarbonate solution (3×200 ml). The organic solvent was removed on a rotary evaporator and the residue was subjected to short column chromatography on silica gel using chloroform and 5-20% methanol/chloroform as eluants. The fractions containing the desired compound, octadec-9-enoic acid{3-[4-(3-octadec-9-enoylamino-propyl)-piperizine-1-yl]-propyl}-amide, were combined and concentrated to obtain an off-white solid (18.28 g, 50% yield). The product was characterized by mass spectrometry.

The diamide compound, octadec-9-enoic acid{3-[4-(3-octadec-9-enylamino-propyl)-piperizine-1-yl]-propyl}-amide (6.2 g) was suspended in anhydrous THF (150 ml) and 100 ml of 1 M lithium aluminium hydride solution in THF was added drop-wise. After the addition was completed, the reaction mix was heated under reflux overnight. More THF (150 ml) was added and the reaction mix was cooled to room temperature. A 15% sodium hydroxide solution (100 ml) was added drop-wise to the mixture and stirred for 2 hours. A saturated sodium bicarbonate solution (250 ml) was added and stirred for approximately 1 hour. The THF layer was decanted and the remaining suspension was exhaustively extracted with chloroform, using TLC to monitor the presence of the desired product in the chloroform layer. The THF and chloroform layers were combined and evaporated to obtain the desired compound, octadec-9-enyl-{3-[4-(3-octadec-9-enylamino-propyl)-piperazin-1-yl]-propyl}-amine (5.11 g, 85% yield). The product was characterized by mass spectrometry.

The amine, octadec-9-enyl-{3-[4-(3-octadec-9-enylamino-propyl)-piperazin-1-yl]-propyl}-amine (5.0 g, 7.1 mmol) was treated with N-(2,3-epoxypropyl)-phthalimide (3.6 g, 17.7 mmol) and lithium perchlorate (1.8 g, 17.0 mmol) in 150 ml reagent alcohol. The mixture was refluxed overnight, cooled and diluted with 400 ml chloroform. The chloroform solution was extracted twice with water (300 ml). The chloroform was removed on a rotary evaporator to obtain the bis-phthalimide adduct as a gum, which was purified by flash chromatography on silica using 1% ethanol in chloroform as eluant, to provide 2.3 g (30% yield) of pure material. The compound was characterized by mass spectrometry.

Hydrazine hydrate (0.5 ml) was added to a solution of the phthalimide (2.25 g) in 100% reagent alcohol (100 ml). The reaction mix was refluxed overnight and cooled to room temperature for about 1 hr. The reaction mix was then cooled at 4° C. overnight and the precipitate obtained by filtration. The solid was washed twice with ethanol chilled to −20° C. (20 ml). The ethanol was removed on a rotary evaporator and the resulting solid dissolved in 300 ml chloroform, filtered and extracted twice with 200 ml water. The chloroform was removed on a rotary evaporator to give 1,4-Bis[(3-(3-amino-2-hydroxypropyl)-oleoylamino)-propyl]piperazine in a quantitative yield ($R_1$, $R_2$=H; $X_1$, $X_2$=CH$_2$; $R_4$, $R_5$=CH$_2$—CH$_2$—CH$_2$; $R_3$, $R_6$=N; $Z_1$, $Z_2$=oleoyl; $W_1$, $W_2$=OH; q, p, m=1; and Y=piperazine). This material was acidified with HCL in dioxane and purified on reverse phase (C-18) flash chromatography using aqueous methanol as eluant and characterized by TLC and mass spectrometry. In this manner compounds with alkyl groups varying in length from $C_{12}$ to $C_{18}$ were synthesized. Specifically the following additional compounds were synthesized. Examples include compounds where: $R_1$, $R_2$=H; $X_1$, $X_2$=CH$_2$; $R_4$, $R_5$=CH$_2$—CH$_2$—CH$_2$; $R_3$, $R_6$=N; $W_1$, $W_2$=OH; q, p, m=1; Y=piperazine; and $Z_1$ and $Z_2$ both are palmityl, myristyl, lauryl or stearyl.

Example 9

Synthesis of 1,4-Bis[(3-(3-aminopropyl)-oleoylamino)propyl]piperazine

The amine, octadec-9-enyl-{3-[4-(3-octadec-9-enylamino-propyl)-piperazin-1-yl]-propyl}-amine (5 g, 7.1 mmol) above was treated with N-(3-bromopropyl)phthalimide (6.78 g, 25 mmol) and diisopropylethylamine (3.7 ml, 21 mmol) in DMF (50 ml). The reaction mixture was heated to 120° C. for 1 hour and then at 95° C. overnight. The solvent was removed by rotary evaporation and the desired phthalamide was isolated by silica flash chromatography using chloroform and methanol/chloroform as eluants. The phthalimide was treated with hydrazine hydrate as described above to obtain 1,4-Bis[(3-(3-aminopropyl)-oleoylamino)propyl]piperazine ($R_1$, $R_2$=H; $X_1$, $X_2$=CH$_2$; $R_4$, $R_5$=CH$_2$—CH$_2$—CH$_2$; $R_3$, $R_6$=N; $Z_1$, $Z_2$=oleoyl; $W_1$, $W_2$=H; q, p, m=1; and Y=piperazine). The compound was characterized by TLC and mass spectrometry. In this manner compounds with alky groups varying in length from $C_{12}$ to $C_{18}$ were synthesized. Examples include compounds where: $R_1$, $R_2$=H; $X_1$, $X_2$=CH$_2$; $R_4$, $R_5$=CH$_2$—CH$_2$—CH$_2$; $R_3$, $R_6$=N; $W_1$, $W_2$=H; q, p, m=1; Y=piperazine; and $Z_1$ and $Z_2$ both are palmityl, myristyl, lauryl or stearyl.

Example 10

Synthesis of 1-amino-3-[(3-amino-2-hydroxy-propyl)-octadec-9-enyl-amino]-propan-2-ol Oleylamine (2.67 g, 10 mmol) was treated with excess N-(2,3-epoxy-propyl)phthalimide (10.72, 40 mmol) and diisopropylethylamine (6.7 ml) in DMF (50 ml). The reaction mix was heated at 95° C. overnight. The solvent was removed by rotary evaporation and the resulting gum was taken up in chloroform (200 ml) and extracted twice with water (200 ml). The chloroform was removed by evaporation and the resulting material subjected to short column chromatography over silica using chloroform as eluant. The desired material thus obtained was treated with hydrazine hydrate as above to obtain 1-amino-3-[(3-amino-2-hydroxy-propyl)-octadec-9-enyl-amino]-propan-2-ol (Compound 6).

Example 11

Formulation of Cationic Lipids into Liposomes

In general, the required amount of the cationic lipid and the co-lipid are weighed and transferred into a round bottom flask. An amount of chloroform that is sufficient to dissolve the lipids is added, followed by sufficient molecular biology-grade water to produce the desired concentration of total lipids/volume (e.g. 2 mg/ml). The chloroform is removed under vacuum in a rotary evaporator. As the chloroform is removed, liposomes are formed in the aqueous medium. The solution becomes opalescent and varies in its turbidity depending on the cationic lipid and co-lipid being formulated More specifically, the HCl salt of 1,4-Bis[(3-(3-aminopropyl)-oleoylamino)-2-hydroxypropyl]piperazine was formulated without a co-lipid and using DOPE or cholesterol as co-lipids. Thus, 14.9 mg of the cationic lipid and 5.1 mg of DOPE (M/M, 2:1) were dissolved in 1 ml chloroform. To the chloroform solution 10 ml of water was added and the heterogeneous solution was evaporated under vacuum on the rotary evaporator. The chloroform was removed leaving a clear opalescent homogenous aqueous solution. The volume was readjusted to 10 ml to obtain a 2 mg/ml solution (129-A). In this manner, the HCl salt of 1,4-Bis[(3-(3-aminopropyl)-oleoylamino)-2-hydroxypropyl]piperazine was formulated with DOPE in a M/M ratio of 4:1 (129-B), with cholesterol in M/M ratio of 2:1 (129-C), 4:1 (129-D) and 1:1 (130-H), and without a co-lipid (129-E).

Example 12

Transfection Protocol

Transfection of CHO-K1 and HEK293 with β-galactosidase reporter plasmid pCMV•SPORT-β-gal was carried out as follows:

Cells were plated in 96-well plates with 100 μl of media containing 10% fetal calf serum the day before transfection such that a desired confluency (70%-95%) was achieved. The following day, lipid and DNA were mixed in Opti-MEM medium to form DNA/lipid complexes. Complexes were formed by adding various amounts of lipids (0.1 to 0.35 μl) to 100 μl of Opti-MEM. DNA (100 ng) was added to 100 μl Opti-MEM. The DNA and lipids solutions were then mixed to form DNA-lipid complexes. The complexes were incubated for at least 20-30 minutes and 20 μl of the complexes was added directly to the cells in 10% serum. Cells were incubated for an additional 24 hours to allow expression of the plasmid. Medium was removed and the cells were lysed in 100-200 μl of lysis buffer. The lysates (20 μl) were assayed for β-gal activity using the enzymatic substrate ONPG. Total activity was determined by reading the OD at 405 nm using a Bio-Rad Benchmark Microplate Spectrophotometer.

Example 13 siRNA Transfection

For siRNA transfection, a 24 well plate is seeded with the appropriate number of cells in serum containing medium a day before transfection such that they are 50 to 60% confluent, and the cells are incubated at 37° C. in a 3-5% $CO_2$ incubator overnight. For each well to be transfected, 25 μl of serum free medium containing 0.1 to 0.4 μl of lipid and 25 μl of serum-free medium containing siRNA is prepared. Final concentration of siRNA is 10 nM. The lipid and siRNA solutions are mixed and incubated at room temperature for 20 minutes. The lipid/siRNA complex (50 μl) is added to the cells in serum-containing medium and the cells are incubated at 37° C. in a $CO_2$ incubator. Gene silencing can be monitored at 24 to 72 hours after transfection.

---

What is claimed is:

1. A compound having the formula:

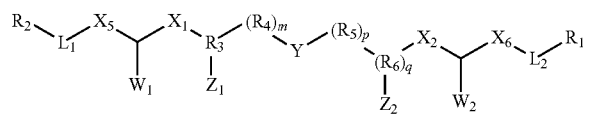

wherein $X_1$ and $X_2$ independently are selected from the group consisting of $(CH_2)_n$, $(CHOH)_n$, and CONH;

$X_5$ and $X_6$ independently are $(CH_2)_{1-6}$;

$W_1$ and $W_2$ independently are selected from the group consisting of, hydrogen, —OH, —O—$(C_1\text{-}C_{18})$ alkyl, —O—$(C_1\text{-}C_{18})$ alkenyl, —O—$(C_1\text{-}C_{18})$ alkynyl, —$NH_2$, —$NH(CH_2)_sCH_3$, —$N((CH_2)_sCH_3)$, —SH, and —NH—$NH_2$;

$R_3$ and $(R_6)_q$ independently are selected from the group consisting of N, NH, CH, and $N(CH_2)_sCH_3$, and q=0-1;

$R_4$ and $R_5$ independently are selected from the group consisting of $(CH_2)_n$, $(CH_2$—CHOH—$CH_2)_n$, $(CHOH)_n$, HNCO, CONH, CO, —O—, —S—, —S—S—, polyamide and an ester linkage;

$L_1$ and $L_2$ independently are selected from the group consisting of —NH—, —O—, —NHCO—, —CONH—, —OCO—, —COO—, —CO—, —S—, —S—S—, —NHC(O)O—, —OC(O)NH—, —NHCONH—, —NHC(=NH)NH—, —NH—NH—, —S(O)— and —$SO_2$—;

Y is a heterocyclic moiety containing at least one amine or amide moiety, wherein the points of attachment of Y are carbon and/or heteroatoms;

$R_1$ and $R_2$ independently are selected from the group consisting of hydrogen, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine amino alcohol, alkyl polyamine, alkenyl polyamine, alkynyl polyamine, spermidine, spermine, carboxy spermine, guanidinium, pyridinium, pyrollidinium, piperidinium, piperazinium, amino acyl, peptidyl, and protein;

$Z_1$ and $Z_2$ independently are selected from the group consisting of long chain straight alkyl, long chain branched alkyl, long chain cycloalkyl, long chain straight chain alkenyl, long chain branched alkenyl, long chain cycloalkenyl, long chain straight chain alkynyl, and long chain branched alkynyl, m, n, p, and s independently are 0-6, with the proviso that when m, n, and p all are 0 then Y is eliminated and $R_3$ is bonded directly to $X_2$.

2. A compound according to claim 1 having the formula:

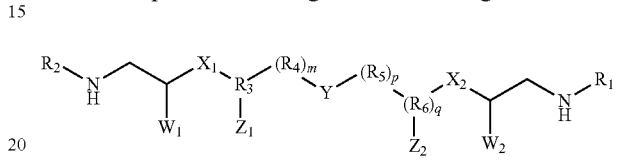

wherein $X_1$, $X_2$, $W_1$, $W_2$, $R_3$, $(R_6)$, $R_4$, $R_5$, Y, $R_1$, $R_2$, $Z_1$, $Z_2$ m, n, p, and s are as defined above.

3. A compound according to claim 1 wherein Y is

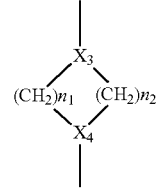

wherein $X_3$ and $X_4$ are independently selected from N and CH and wherein $n_1$ and $n_2$ independently are 1-10.

4. A compound according to claim 3, wherein $X_3$ and $X_4$ are N and $n_1$ and $n_2$ independently are 1-10.

5. The compound according to claim 1, wherein $L_1$ and $L_2$ independently are selected from the group consisting of —NH—, —O—, —NHCO—, —CONH—, —NHC(O)O—, —OC(O)NH—, —NHCONH—, —NHC(=NH)NH—, —S(O)— and —$SO_2$—.

6. The compound according to claim 5, wherein $L_1$ and $L_2$ independently are selected from the group consisting of —NH—, —NHCO—, —CONH—, —NHC(O)O—, and —OC(O)NH—.

7. The compound according to claim 2, wherein Y is

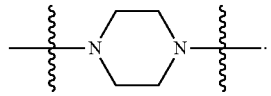

8. The compound according to claim 7, wherein $R_4$ and $R_5$ independently are $(CH_2)_n$.

9. The compound according to claim 7, wherein $R_4$ and $R_5$ independently are $(CH_2$—CHOH—$CH_2)_n$.

10. The compound according to claim 8 wherein $R_4$ and $R_5$ are $(CH_2)_3$.

11. The compound according to claim 9 wherein $R_4$ and $R_5$ are $(CH_2$—CHOH—$CH_2)$.

12. The compound according to claim 10,
wherein $R_1$ and $R_2$ are H; $X_1$ and $X_2$ are $CH_2$; $R_3$ and $R_6$ are N; $W_1$ and $W_2$ are H or OH; q, p, and m are 1;

and $Z_1$ and $Z_2$ independently are selected from the group consisting of oleoyl, oleyl, palmityl, myristyl, stearyl, and lauryl.

13. The compound according to claim 11,
wherein $R_1$ and $R_2$ are H; $X_1$ and $X_2$ are $CH_2$; $R_3$ and $R_6$ are N; $W_1$ and $W_2$ are H or OH; q, p, and m are 1;
and $Z_1$ and $Z_2$ independently are selected from the group consisting of oleoyl, oleyl, palmityl, myristyl, stearyl, and lauryl.

14. A composition comprising a compound according to claim 1 and a co-lipid- that is neutral, positively charged or negatively charged.

15. The composition according to claim 14 wherein said co-lipid is DOPE or cholesterol.

16. The composition according to claim 14, further comprising a macromolecule.

17. The composition according to claim 16 wherein said macromolecule is a nucleic acid.

18. The composition according to claim 17, wherein said nucleic acid comprises a DNA molecule.

19. The composition according to claim 17, wherein said DNA molecule is a double stranded DNA molecule encoding an RNA molecule that is self complementary and that forms a region of double stranded RNA.

20. The composition according to claim 17, wherein said nucleic acid comprises a double stranded RNA molecule.

21. The composition according to claim 17 wherein said RNA molecule is an siRNA.

22. The composition according to claim 16, further comprising a eukaryotic cell.

23. The composition according to claim 22, wherein said cell is a mammalian cell.

24. A method of introducing a macromolecule into a cell, comprising contacting a eukaryotic cell with a composition according to claim 16.

* * * * *

SEQUENCE LISTING

```
<160> NUMBER OF SEQ ID NOS: 33

<210> SEQ ID NO 1
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Leu Arg Met Pro Pro Gly Ser Cys Asn Gly Ala Thr Ala Val Phe
 1               5                  10                  15

Gly Asn Val His Cys Gln Ala Ala Gln Asn Thr Ala Gly Gly Asp Leu
            20                  25                  30

Gln Ala Thr Ser Ser Ile Ile Ala
        35                  40

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Pro Arg Met Pro Pro Gly Ser Cys Asn Gly Ala Thr Ala Val Phe
 1               5                  10                  15

Gly Asn Val His Cys Gln Ala Ala Gln Asn Thr Ala Gly Gly Asp Leu
            20                  25                  30

Gln Ala Thr Ser Ser Ile Ile Ala
        35                  40

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ser Gly Asp Cys Ala Gly Leu Val Ser Val Phe Gly Ser Val His
 1               5                  10                  15

Cys Gln Ser Ser Lys Asn Lys Ala Gly Gly Asp Leu Gln Ala Thr Ser
            20                  25                  30

Ile Leu Thr Thr Tyr Trp Pro His
        35                  40

<210> SEQ ID NO 4
<211> LENGTH: 40
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Met Ser Ser Asp Cys Ala Lys Ile Val Ser Val Phe Gly Ser Val His
1               5                   10                  15

Cys Gln Ser Ser Lys Asn Ser Ala Gly Gly Asp Leu Gln Ala Thr Ser
            20                  25                  30

Val Phe Thr Thr Tyr Trp Pro His
        35                  40

<210> SEQ ID NO 5
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Gly Gln Arg His Ser Ile Val Gln Pro Pro Ala Pro Pro Pro Asn
1               5                   10                  15

Ala Phe Val Glu Ile Val Ser Ser Ser Thr Gly Ile Ile Ala Val
            20                  25                  30

Gly Ile Phe Ala Phe Ile Phe Ser
        35                  40

<210> SEQ ID NO 6
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile
        35                  40

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Met Pro Pro Gly Ser Cys Asn Gly Ala Thr Ala Val Phe Gly Asn
1               5                   10                  15

Val His

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 8

Gly Asp Cys Ala Gly Leu Val Ser Val Phe Gly Ser Val His
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Asp Cys Ala Lys Ile Val Ser Val Phe Gly Ser Val His
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Arg His Ser Ile Val Gln Pro Pro Ala Pro Pro Asn Ala Phe
1               5                   10                  15

Val Glu Ile Val Ser
            20

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Pro Ser Asn Phe Val Asn His Ala Pro Gly Glu Ala Ile Val
1               5                   10                  15

Thr

<210> SEQ ID NO 12
<211> LENGTH: 95
<212> TYPE: PRT
<213> ORGANISM: Nelson Bay Reovirus

<400> SEQUENCE: 12

Met Ser Ser Asp Cys Ala Lys Ile Val Ser Val Phe Gly Ser Val His
1               5                   10                  15

Cys Gln Ser

-continued

<210> SEQ ID NO 13
<211> LENGTH: 98
<212> TYPE: PRT
<213> ORGANISM: Avian Reovirus
<220> FEATURE:
<221> NAME/KEY: MOD_RES
<222> LOCATION: (15)
<223> OTHER INFORMATION: Ile or Val

<400> SEQUENCE: 13

Met Leu Arg Met Pro Pro Gly Ser Cys Asn Gly Ala Thr Ala Xaa Phe
1               5                   10                  15

Gly Asn Val His Cys Gln Ala Ala Gln Asn Thr Ala Gly Gly Asp Leu
            20                  25                  30

Gln Ala Thr Ser Ser Ile Ile Ala Tyr Trp Pro Tyr Leu Ala Ala Gly
        35                  40                  45

Gly Gly Phe Leu Leu Ile Val Ile Ile Phe Ala Ile Leu Tyr Cys Cys
    50                  55                  60

Lys Ala Lys Val Lys Ala Asp Ala Ala Arg Ser Val Phe His Arg Glu
65                  70                  75                  80

Leu Val Ala Leu Ser Ser Gly Lys His Asn Ala Met Ala Pro Pro Tyr
                85                  90                  95

Asn Val

<210> SEQ ID NO 14
<211> LENGTH: 98
<212> TYPE: PRT
<213> ORGANISM: Avian Reovirus

<400> SEQU

<223> OTHER INFORMATION: Description of Artificial Sequence: Synthetic
      peptide

<400> SEQUENCE: 16

Met Leu Arg Met Pro Pro Gly Ser Cys Asn Gly Ala Thr Ala Ile Phe
 1               5                  10                  15

Gly Asn Val His Cys Gln Ala Ala Gln Asn Thr Ala Gly Gly Asp Leu
            20                  25                  30

Gln Ala Thr Ser Ser Ile Ile Ala
        35                  40

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Met Pro Pro Gly Ser Cys Asn Gly Ala Thr Ala Val Phe Gly Asn
 1               5                  10                  15

Val His Cys Gln Ala Ala Gln Asn Thr Ala Gly Gly Asp Leu Gln Ala
            20                  25                  30

Thr Ser Ser Ile Ile Ala
        35

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Met Pro Pro Gly Ser Cys Asn Gly Ala Thr Ala Ile Phe Gly Asn
 1               5                  10                  15

Val His Cys Gln Ala Ala Gln Asn Thr Ala Gly Gly Asp Leu Gln Ala
            20                  25                  30

Thr Ser Ser Ile Ile Ala
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Asp Cys Ala Gly Leu Val Ser Val Phe Gly Ser Val His Cys Gln
 1               5                  10                  15

Ser Ser Lys Asn Lys Ala Gly Gly Asp Leu Gln Ala Thr Ser Ile Leu
            20                  25                  30

Thr Thr Tyr Trp Pro His
        35

<210> SEQ ID NO 20
<211> LENGTH: 38
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Ser Asp Cys Ala Lys Ile Val Ser Val Phe Gly Ser Val His Cys Gln
1               5                   10                  15

Ser Ser Lys Asn Ser Ala Gly Gly Asp Leu Gln Ala Thr Ser Val Phe
            20                  25                  30

Thr Thr Tyr Trp Pro His
            35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Pro Ser Asn Phe Val Asn His Ala Pro Gly Glu Ala Ile Val
1               5                   10                  15

Thr Gly Leu Glu Lys Gly Ala Asp Lys Val Ala Gly Thr Ile Ser His
            20                  25                  30

Thr Ile Trp Glu Val Ile
            35

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Arg His Ser Ile Val Gln Pro Pro Ala Pro Pro Pro Asn Ala Phe
1               5                   10                  15

Val Glu Ile Val Ser Ser Ser Thr Gly Ile Ile Ile Ala Val Gly Ile
            20                  25                  30

Phe Ala Phe Ile Phe Ser
            35

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Met Pro Pro Gly Ser Cys Asn Gly Ala Thr Ala Ile Phe Gly Asn
1               5                   10                  15

Val His

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 24

Gly Asp Cys Ala Gly Leu Val Ser Val Phe Gly Ser Val His Cys Gln
1               5                   10                  15

Ser Ser

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Asp Cys Ala Lys Ile Val Ser Val Phe Gly Ser Val His Cys Gln
1               5                   10                  15

Ser Ser

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Arg His Ser Ile Val Gln Pro Pro Ala Pro Pro Pro Asn Ala Phe
1               5                   10                  15

Val Glu

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Pro Ser Asn Phe Val Asn His Ala Pro Gly Glu Ala Ile Val
1               5                   10                  15

Thr Gly

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Met Pro Pro Gly Ser Cys Asn Gly Ala Thr Ala Val Phe Gly Asn
1               5                   10                  15

Val His Lys Lys Lys Lys Lys Lys Lys Lys Lys Lys Lys Lys Lys Lys
                20                  25                  30

Lys Lys

<210> SEQ ID NO 29
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 29

Arg Met Pro Pro Gly Ser Cys Asn Gly Ala Thr Ala Ile Phe Gly Asn
 1               5                  10                  15

Val His Lys Lys Lys Lys Lys Lys Lys Lys Lys Lys Lys Lys Lys Lys
                20                  25                  30

Lys Lys

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Asp Cys Ala Gly Leu Val Ser Val Phe Gly Ser Val His Cys Gln
 1               5                  10                  15

Ser Ser Lys Lys Lys Lys Lys Lys Lys Lys Lys Lys Lys Lys Lys Lys
                20                  25                  30

Lys Lys

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Asp Cys Ala Lys Ile Val Ser Val Phe Gly Ser Val His Cys Gln
 1               5                  10                  15

Ser Ser Lys Lys Lys Lys Lys Lys Lys Lys Lys Lys Lys Lys Lys Lys
                20                  25                  30

Lys Lys

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Arg His Ser Ile Val Gln Pro Pro Ala Pro Pro Asn Ala Phe
 1               5                  10                  15

Val Glu Lys Lys Lys Lys Lys Lys Lys Lys Lys Lys Lys Lys Lys Lys
                20                  25                  30

Lys Lys

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 33

Ser Gly Pro Ser Asn Phe Val Asn His Ala Pro Gly Glu Ala Ile Val
1               5                   10                  15

Thr Gly Lys Lys Lys Lys Lys Lys Lys Lys Lys Lys Lys Lys Lys Lys
            20                  25                  30

Lys Lys
```